(12) United States Patent
Haldar et al.

(10) Patent No.: US 10,081,655 B2
(45) Date of Patent: Sep. 25, 2018

(54) CATIONIC ANTIBACTERIAL COMPOSITION

(71) Applicant: JAWAHARLAL NEHRU CENTRE FOR ADVANCED SCIENTIFIC RESEARCH, Bangalore, Karnataka (IN)

(72) Inventors: Jayanta Haldar, Bangalore (IN); Yarlagadda Venkateswarlu, Bangalore (IN); Padma Akkapeddi, Bangalore (IN)

(73) Assignee: JAWAHARLAL NEHRU CENTRE FOR ADVANCED, Bangalore, Karnataka (IN)

( * ) Notice: Subject to any disclaimer, the term of this patent is extended or adjusted under 35 U.S.C. 154(b) by 180 days.

(21) Appl. No.: 14/357,928

(22) PCT Filed: Nov. 13, 2012

(86) PCT No.: PCT/IB2012/056373
§ 371 (c)(1),
(2) Date: May 13, 2014

(87) PCT Pub. No.: WO2013/072838
PCT Pub. Date: May 23, 2013

(65) Prior Publication Data
US 2014/0308347 A1    Oct. 16, 2014

(30) Foreign Application Priority Data
Nov. 14, 2011  (IN) .......................... 3889/CHE/2011

(51) Int. Cl.
*C07K 9/00* (2006.01)
*A61K 38/00* (2006.01)

(52) U.S. Cl.
CPC .............. *C07K 9/008* (2013.01); *A61K 38/00* (2013.01); *Y02A 50/473* (2018.01)

(58) Field of Classification Search
CPC ................................ A61K 38/00; C07K 9/008
See application file for complete search history.

(56) References Cited

U.S. PATENT DOCUMENTS

| 2005/0250677 | A1 | 11/2005 | Balzarini et al. |
| 2008/0097078 | A1 | 4/2008 | Arimoto et al. |
| 2014/0171357 | A1* | 6/2014 | Radhakrishnan ...... C07K 9/008 514/1.3 |

FOREIGN PATENT DOCUMENTS

| EP | 1818340 A1 | 8/2007 |
| WO | WO-2004019970 A2 | 3/2004 |

OTHER PUBLICATIONS

Balzarini et al., Antiviral Research 72 (2006) 20-33.*
Kell et al., ACS Nano, vol. 2, No. 9, 1777-1788 (2008).*
Nicolosi D et al: "Encapsulation in fusogenic liposomes broadens the spectrum of action of vancomycin against Gram-negative bacteria", International Journal of Antimicrobial Agents, Elsevier Science, Amsterdam, NL, vol. 35, No. 6, Jun. 1, 2010 (Jun. 1, 2010), pp. 553-558, XP027000734, ISSN: 0924-8579 [retrieved on Apr. 13, 2010] abstract.

* cited by examiner

*Primary Examiner* — Robert S Cabral
(74) *Attorney, Agent, or Firm* — Harness, Dickey & Pierce, P.L.C.

(57) ABSTRACT

The present invention relates to compounds that are cationic vancomycin analogs and their compositions. Method of making the compounds and their use as medicament for the treatment of bacterial infection are also disclosed.

20 Claims, 10 Drawing Sheets
(7 of 10 Drawing Sheet(s) Filed in Color)

Figure 6:
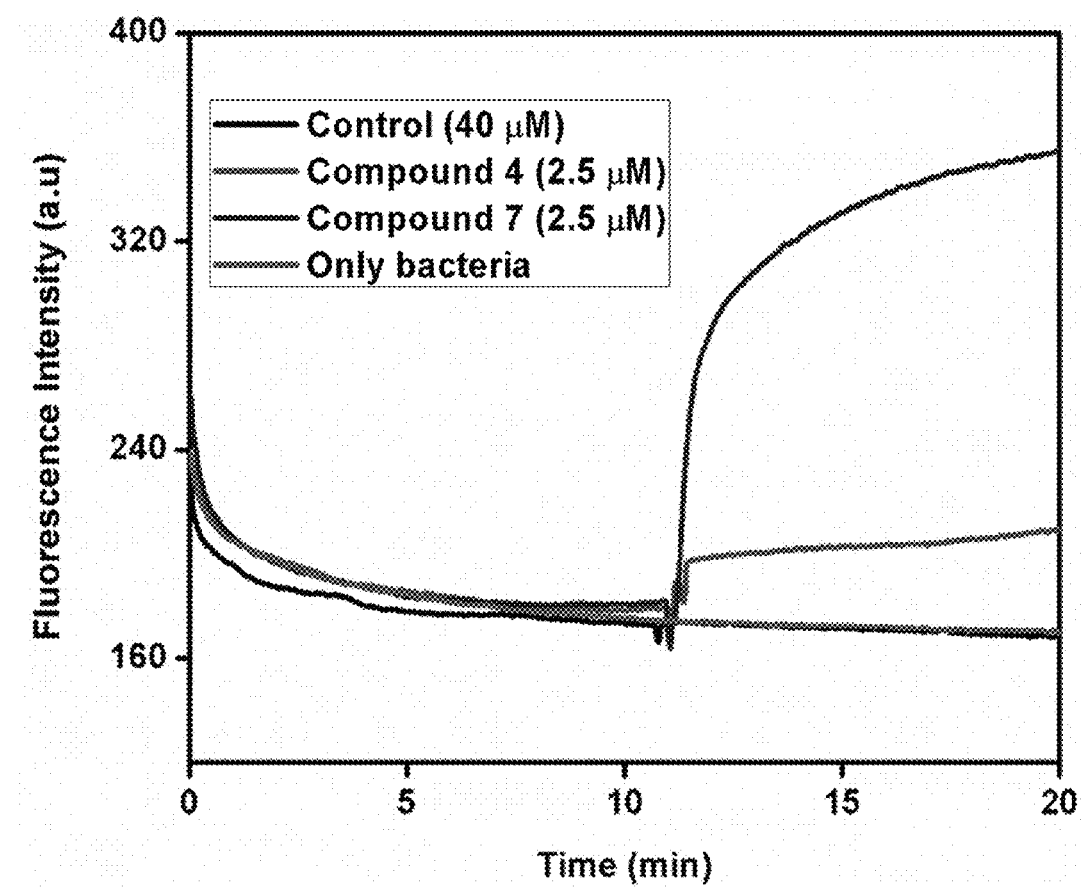

Figure 6 : *In-vivo* antibacterial efficacy of Vancomycin (Van) and derivative 4 (Van-$C_8$) against MRSA. Red arrow indicates the amount of bacteria used for infection.

CATIONIC ANTIBACTERIAL COMPOSITION

CROSS-REFERENCE TO RELATED APPLICATIONS

This application is a 371 U.S. National Stage of International Application No. PCT/IB2012/056373, filed Nov. 13, 2012, which claims priority to Indian Patent Application 3889/CHE/2011, filed Nov. 14, 2011. The disclosures of the above application are incorporated herein by reference.

FIELD OF DISCLOSURE

The present disclosure relates to the field of medicinal chemistry and more particularly to the development of antibacterial compounds. The present invention relates to the synthesis and characterization of cationic antibacterial compounds designed to exhibit antibacterial activity, for example, against a Gram-positive bacteria and/or a Gram-negative bacteria.

BACKGROUND

Bacterial infections are a major global health hazard affecting millions of people worldwide. Many antibacterial drugs and articles have been developed over the years for better treatment or prevention of bacterial infections. For example, Vancomycin, a narrow spectrum antibacterial compound, is active against Gram-positive bacteria. Vancomycin inhibits bacterial cell wall synthesis by binding to the peptidoglycan peptide terminus D-Ala-D-Ala found in bacterial cell wall precursors, sequestering the substrate from transpeptidase and inhibiting cell wall cross-linking. However, over the years, many Gram-positive bacteria have acquired resistance to Vancomycin by modifying their peptidoglycan terminus, changing from D-Ala-D-Ala to D-Ala D-Lac. Significant efforts have been directed toward the discovery of next-generation glycopeptide antibiotics that address the emerging drug-resistance of bacteria, especially the vancomycin resistance.

The options for treating drug-resistant bacteria have not yet realized successfully and the emergence of drug-resistant bacteria strains is on the increase. Thus there is continuous need to identify and/or develop new compounds and/or derivatives that has improved activity against drug-resistant bacterial strains.

The present invention relates to cationic compounds that exhibit a wide spectrum of antibacterial activity against both wild-type and drug-resistant bacteria. The disclosed compounds and compositions comprising the disclosed compounds are active against both Gram-positive bacteria and Gram-negative bacteria.

SUMMARY OF INVENTION

In some embodiments the invention describes a compound of formula I:

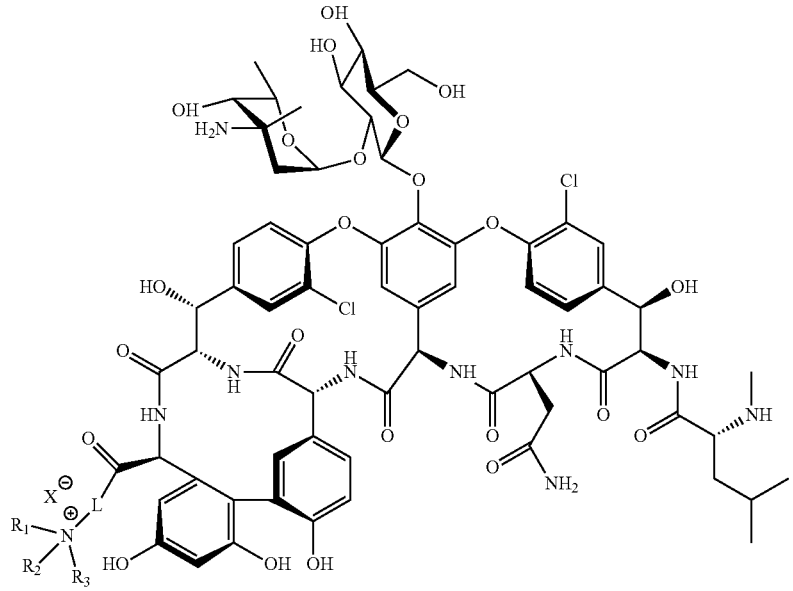

Formula I wherein L is a $C_2$-$C_{22}$ aliphatic radical or a $C_3$-$C_{22}$ aromatic radical; $R_1$, $R_2$, and $R_3$ are, independently at each occurrence, a $C_1$-$C_{40}$ aliphatic radical, or a $C_3$-$C_{40}$ aromatic radical; and at least one of $R_1$, $R_2$, or $R_3$ includes at least 2 carbon atoms.

Another embodiment of the invention provides the compound of Formula I, a pharmaceutically acceptable salt, or any composition thereof for use as medicament. In some embodiments, the invention provides the compound of Formula I, a pharmaceutically acceptable salt or any composition thereof for use in treatment of a bacterial infection.

Yet another embodiment of the invention provides the compound of Formula II, a pharmaceutically acceptable salt, or any composition thereof for use as medicament. In some embodiments, the invention provides the compound of Formula II, a pharmaceutically acceptable salt or any composition thereof for use in treatment of a bacterial infection.

Still another embodiment of the invention provides a method for treatment of a bacterium in a subject the method including steps of administering to the subject an effective amount of compound of Formula I, pharmaceutically acceptable salt, or any composition thereof.

BRIEF DESCRIPTION OF ACCOMPANYING FIGURES

The patent or application file contains at least one drawing executed in color. Copies of this patent or patent application publication with color drawing(s) will be provided by the Office upon request and payment of the necessary fee.

Figure 1:
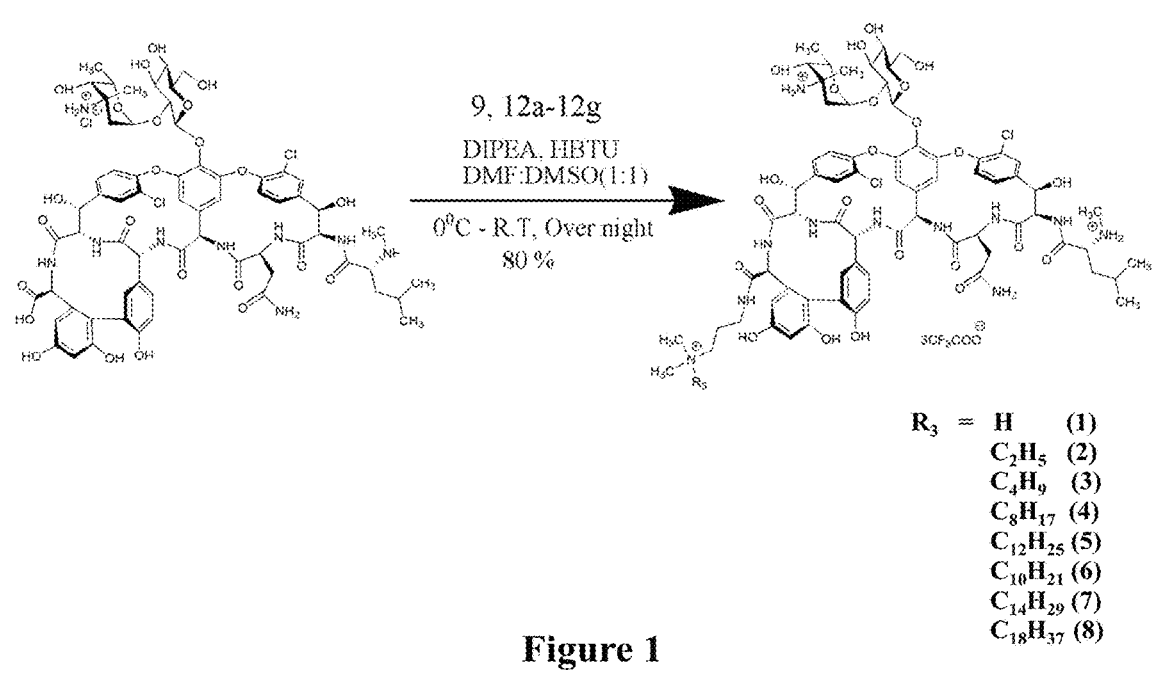

The features of the present disclosure will become more fully apparent from the following description taken in conjunction with the accompanying drawings. Understanding that the drawings depict only several embodiments in accordance with the disclosure, and is therefore, not to be considered limiting of its scope. The disclosure will be described with additional specificity and detail through use of the accompanying drawing:

FIG. 1 relates to synthesis of cationic antibacterial compounds (1-8).

Figure 2:
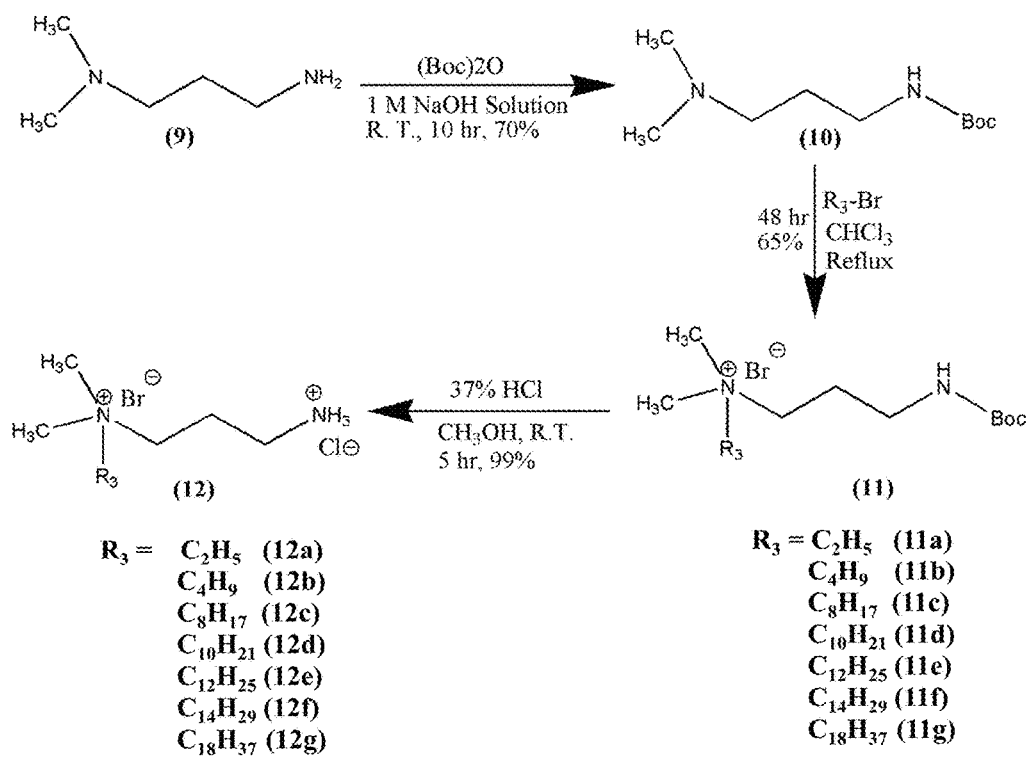

FIG. 2 relates to synthesis of cationic moieties (12a-12g).

Figure 3:
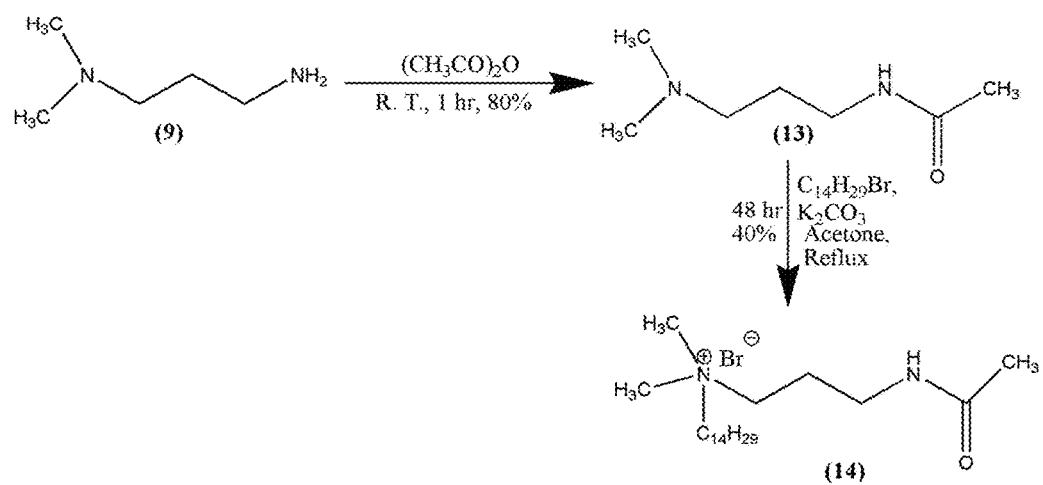

FIG. 3 relates to synthesis of compound 14.

Figure 4:
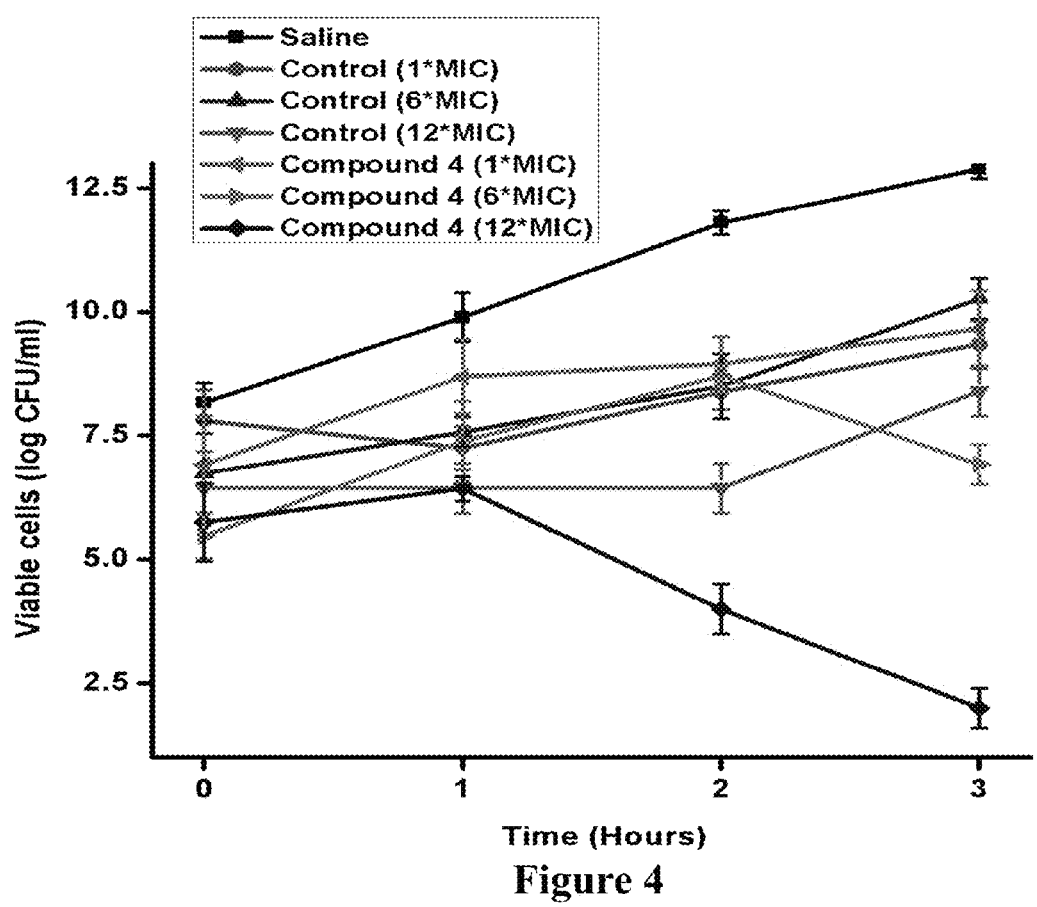

FIG. 4 relates to time-kill kinetic study of compound (4) and control (vancomycin) against methicillin-resistant *Staphylococcus aureus* (MRSA).

Figure 5:
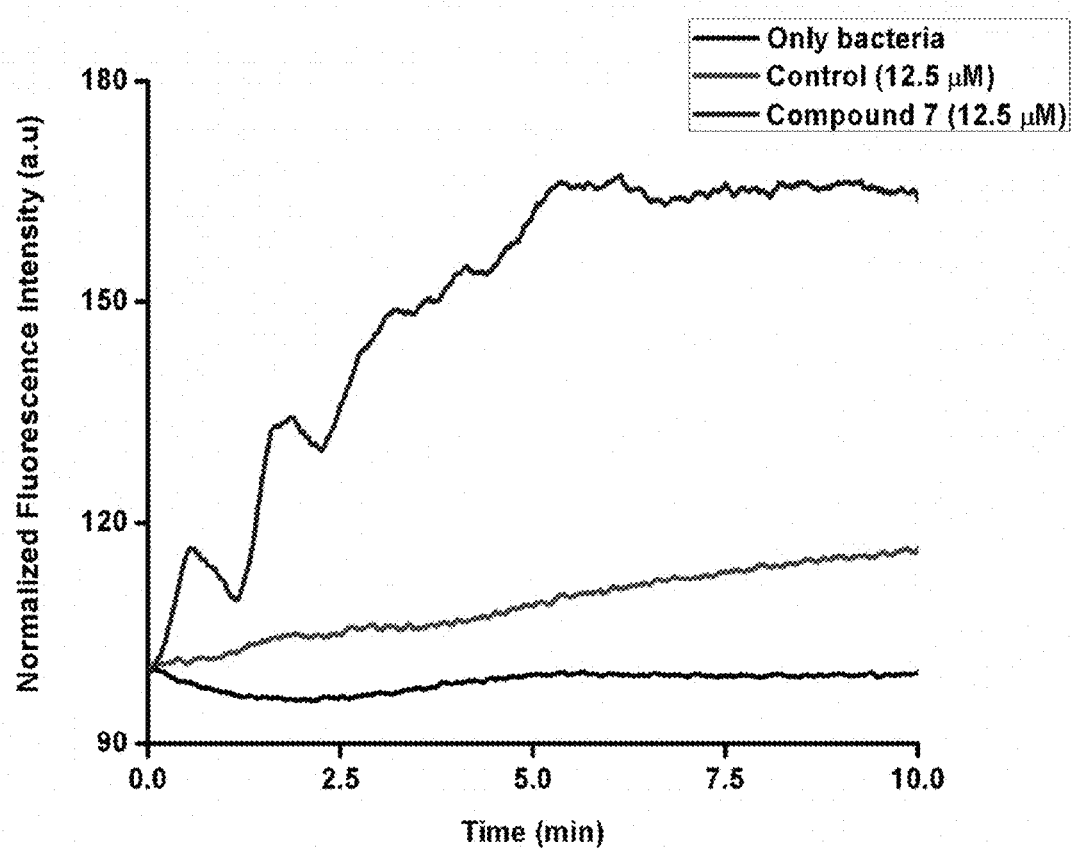

FIG. 5 relates to outer membrane permeabilization study of compound (7) and control against *E. coli*.

FIG. 6 relates to cytoplasmic depolarization study of compounds (4 and 7) and control against methicillin-sensitive *Staphylococcus aureus* (MSSA).

Figure 7:
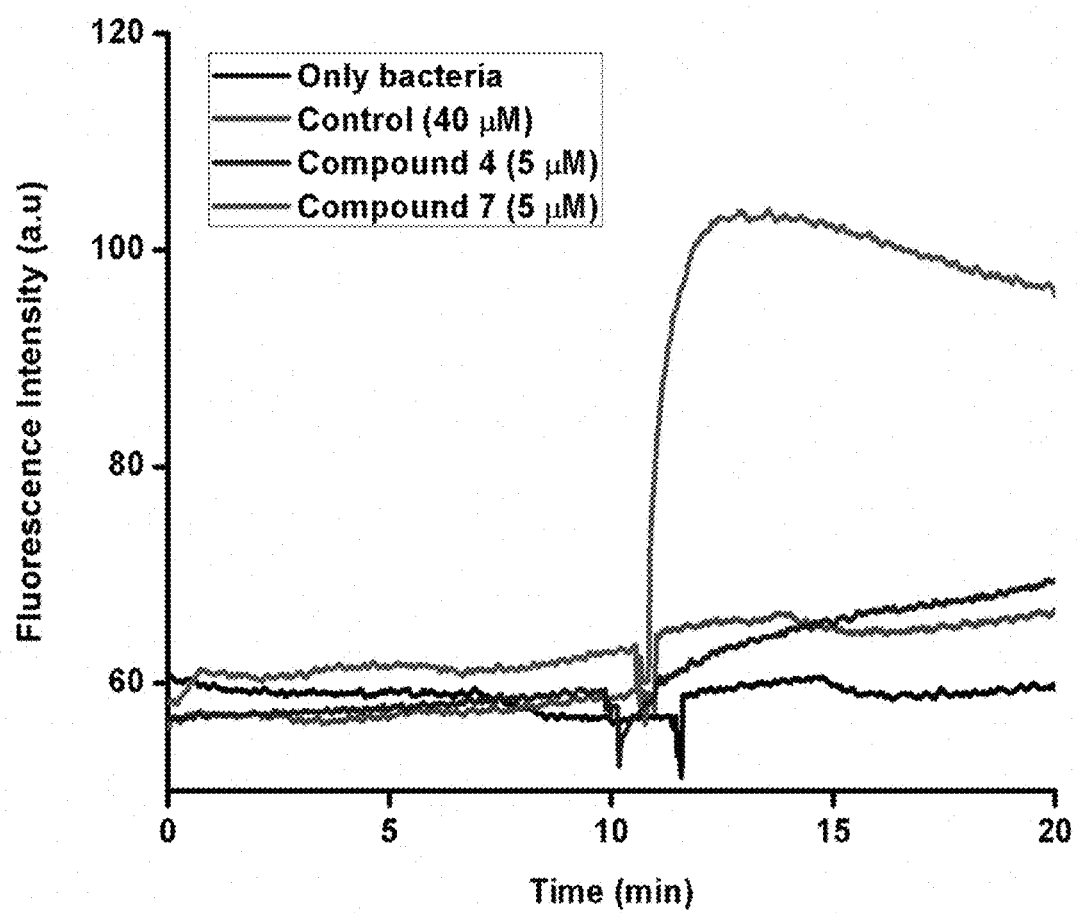

FIG. 7 relates to cytoplasmic depolarization study of compounds (4 and 7) and control against *E. coli*.

Figure 8:
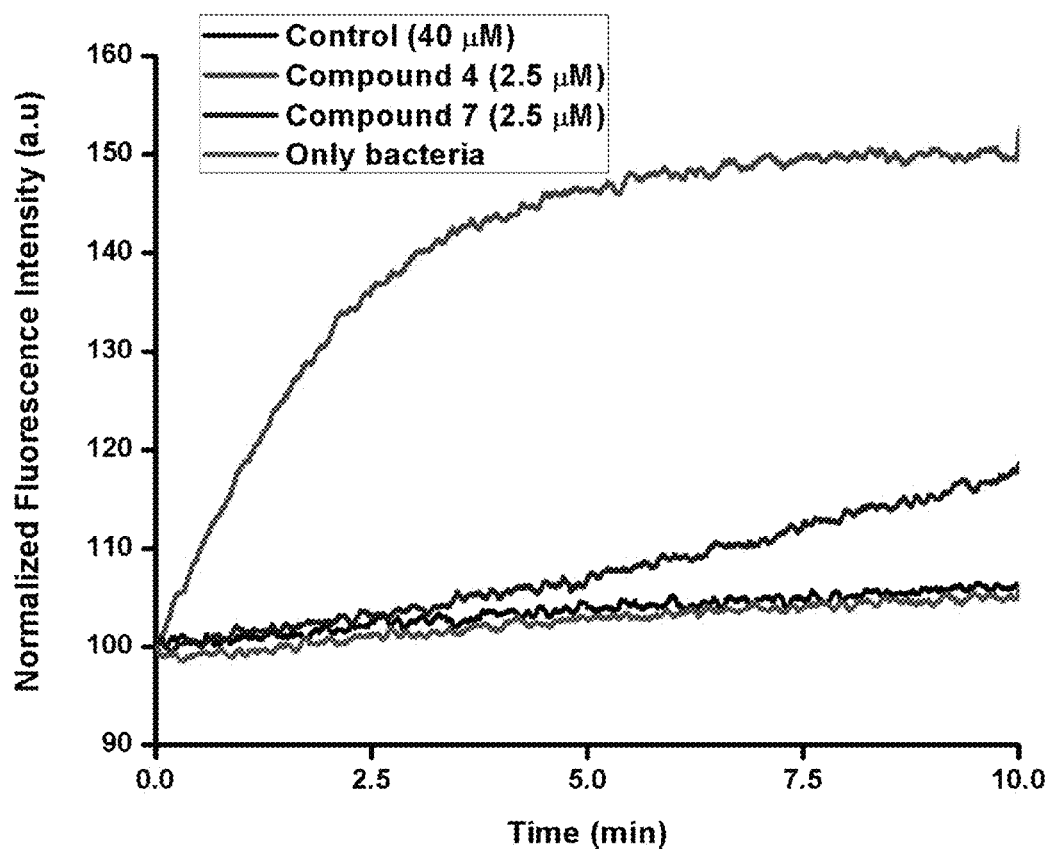

FIG. 8 relates to inner membrane permeabilization study of compounds (4 and 7) and control against MSSA.

Figure 9:
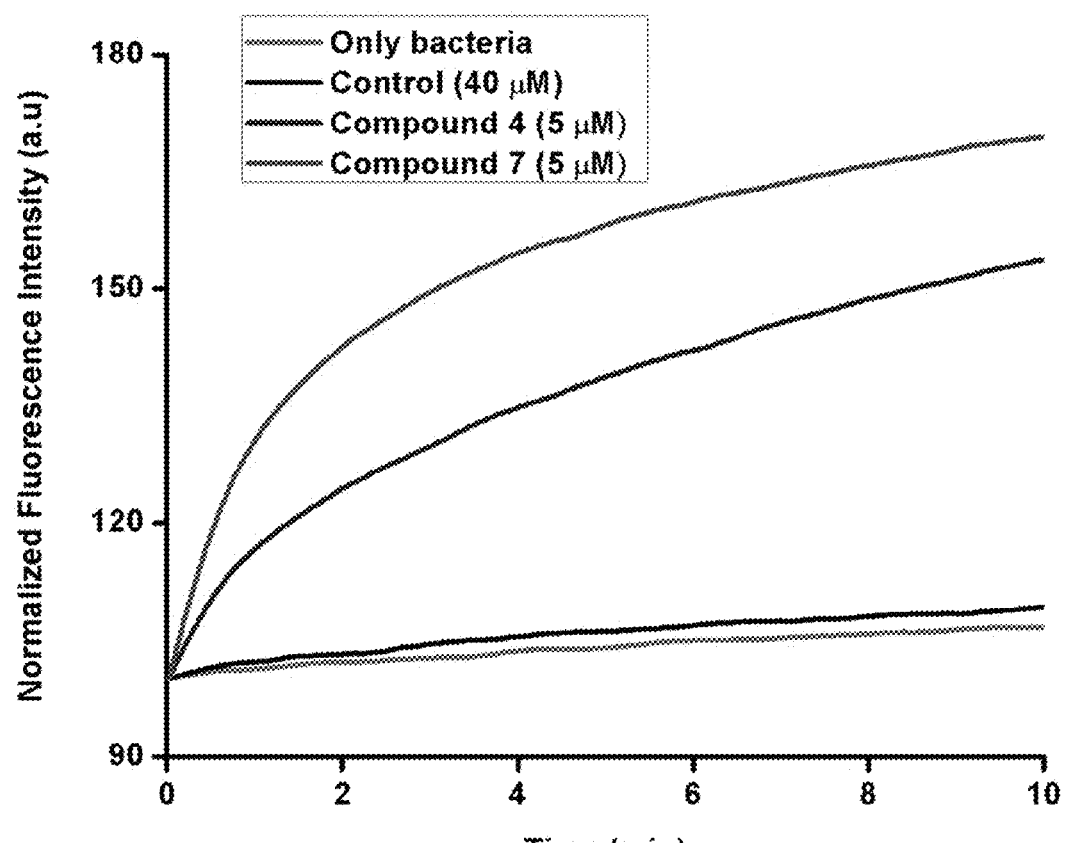

FIG. 9 relates to inner membrane permeabilization study of compounds (4 and 7) and control against *E. coli*.

Figure 10:
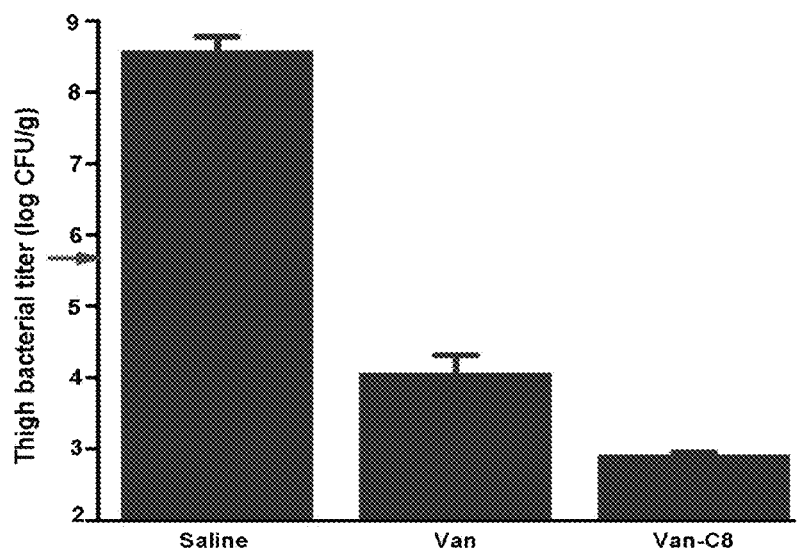
Figure 10:

FIG. 10 relates to In-vivo antibacterial efficacy of compound (4) and control against MRSA. Red arrow indicates the amount of bacteria used for infection.

DETAILED DESCRIPTION OF INVENTION

The present disclosure relates to a compound of formula I:

wherein,

L is a $C_2$-$C_{22}$ aliphatic radical or a $C_3$-$C_{22}$ aromatic radical; $R_1$, $R_2$ and $R_3$ are, independently at each occurrence, a $C_1$-$C_{40}$ aliphatic radical or a $C_3$-$C_{40}$ aromatic radical; and at least one of $R_1$, $R_2$, or $R_3$ comprises at least 2 carbon atoms.

In an embodiment of the disclosure, L is a $C_2$-$C_8$ aliphatic radical.

In another embodiment of the disclosure, $R_1$, $R_2$, and $R_3$ are, independently at each occurrence, a $C_2$-$C_{24}$ aliphatic radical.

In yet another embodiment of the disclosure, $R_1$ and $R_2$ are methyl radicals, and wherein $R_3$ is a $C_2$-$C_{24}$ aliphatic radical.

In still another embodiment of the disclosure, $R_3$ is a hydrophobic moiety.

In still another embodiment of the disclosure, $R_3$ is a $C_8$-$C_{14}$ aliphatic radical.

In still another embodiment of the disclosure, L is a $C_3$ aliphatic radical.

In still another embodiment of the disclosure, $R_3$ is a saturated alkyl radical or an unsaturated alkyl radical.

In still another embodiment of the disclosure, at least one of $R_1$, $R_2$, or $R_3$ comprises a structural moiety selected from the group consisting of:

wherein, P is a $C_1$-$C_{24}$ aliphatic saturated radical or a $C_2$-$C_{24}$ aliphatic unsaturated radical, and n is an integer ranging from 1 to 4, wherein, P is a $C_1$-$C_{24}$ aliphatic saturated radical or a $C_2$-$C_{24}$ aliphatic unsaturated radical, and n is an integer ranging from 1 to 4, Formula I

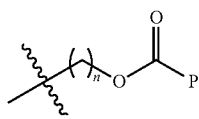

wherein, P is a $C_1$-$C_{24}$ aliphatic saturated radical or a $C_2$-$C_{24}$ aliphatic unsaturated radical, and n is an integer ranging from 1 to 4,

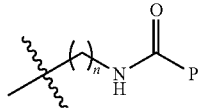

wherein, P is a $C_1$-$C_{24}$ aliphatic saturated radical or a $C_2$-$C_{24}$ aliphatic unsaturated radical, and n is an integer ranging from 1 to 4,

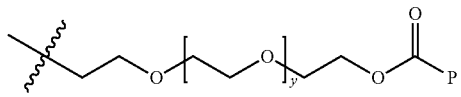

wherein, P is a $C_1$-$C_{24}$ aliphatic saturated radical or a $C_2$-$C_{24}$ aliphatic unsaturated radical, and y is an integer ranging from 0 to 3,

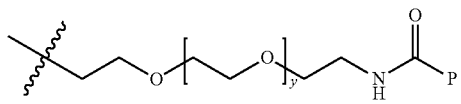

wherein, P is a $C_1$-$C_{24}$ aliphatic saturated radical or a $C_2$-$C_{24}$ aliphatic unsaturated radical, and y is an integer ranging from 0 to 3,

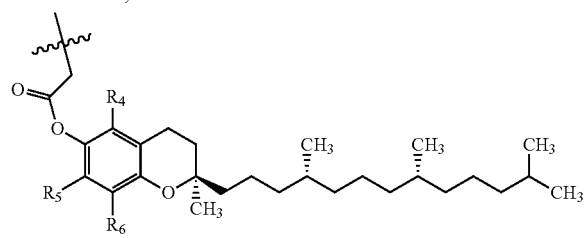

wherein, $R_4$=$R_5$=$R_6$=—$CH_3$ or $R_4$=$R_6$=—$CH_3$ and $R_5$=—H or $R_4$=—H and $R_5$=$R_6$=—$CH_3$ or $R_4$=$R_5$=—H, $R_6$=—$CH_3$,

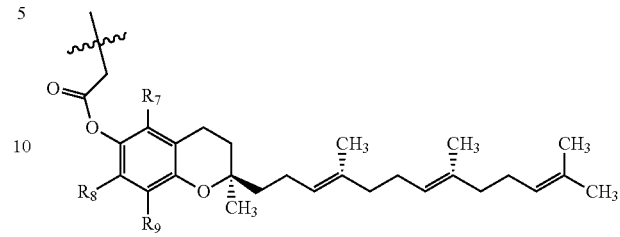

wherein, $R_7$=$R_8$=$R_9$=—$CH_3$ or $R_7$=$R_9$=—$CH_3$ and $R_8$=—H or $R_7$=—H and $R_8$=$R_9$=—$CH_3$ or $R_7$=$R_8$=—H and $R_9$=—$CH_3$,

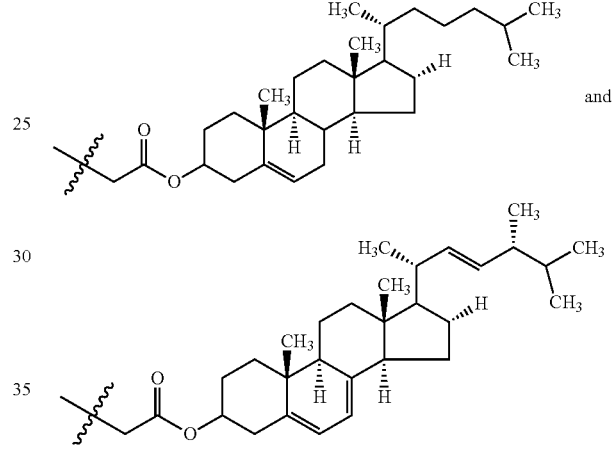

and

The present disclosure also relates to a compound of formula II:

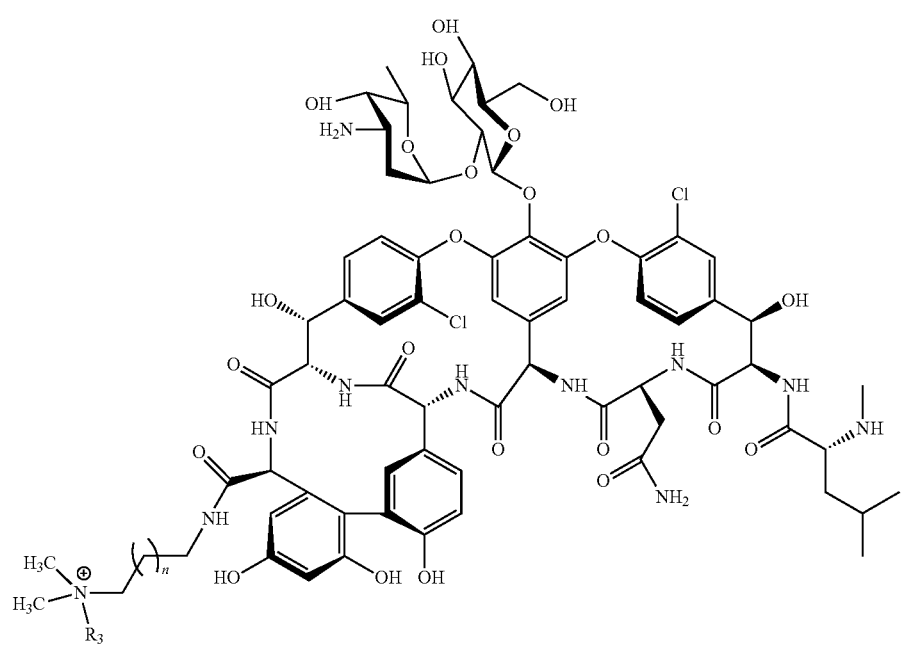

Formula II wherein, $R_3$ is an aliphatic saturated radical represented by formula $C_mH_{2m+1}$, wherein m is an integer ranging from 8 to 14, and wherein n is an integer ranging from 0 to 3.

The present disclosure also relates to a pharmaceutically acceptable salt of the compound of any of claims 1-10.

The present disclosure also relates to a composition comprising:
the compound of any of claims 1-10 or the pharmaceutically acceptable salt of claim 11; and
a pharmaceutically acceptable excipient.

In an embodiment of the disclosure, the pharmaceutically acceptable excipient is selected from the group consisting of sugar, starch, cellulose, malt, gelatine, talc, cocoa butter, suppository wax, oil, glycol, ester, agar, buffering agent, alginic acid, pyrogen-free water, isotonic saline, Ringer's solution, alcohol, lipid, surfactant, coloring agent, releasing agent, coating agent, sweetening agent, flavouring agent, perfuming agent, preservatives, antioxidants and combinations thereof, and their derivatives.

The present disclosure also relates to a method of making a lipophilic quarternary ammonium derivative of vancomycin comprising:
activating a carboxylic acid moiety of vancomycin to generate an activated vancomycin; and
reacting the activated vancomycin with a primary amine comprising a lipophilic quarternary ammonium moiety.

In an embodiment of the disclosure, the compound or the pharmaceutically acceptable salt or the composition as mentioned above is used as medicament or is used in treatment of a bacterial infection or is used in treatment of a bacterial infection caused by a Gram-positive bacterium or a Gram-negative bacterium.

In another embodiment of the disclosure, the compound or the pharmaceutically acceptable salt or the composition as mentioned above is used in treatment of a bacterial infection, wherein the bacterium comprises a drug-resistant bacterium or a vancomycin-resistant bacterium or a methicillin-resistant bacterium or a vancomycin-resistant *Staphylococcus aureus*, a vancomycin-resistant *Enterococcus faecium* or a methicillin-resistant *Staphylococcus aureus*.

In yet another embodiment of the disclosure, the compound or the pharmaceutically acceptable salt or the composition as mentioned above is used in treatment of an *E. coli* infection.

The present disclosure also relates to a method for treatment of bacterial infection in a subject comprising:
administering to the subject an effective amount of the compound of any of claims 1-10, the pharmaceutically acceptable salt of claim 11, or the composition of any of claims 12-13.

In an embodiment of the disclosure, the bacterial infection is caused by a Gram-positive bacterium or a Gram-negative bacterium.

In another embodiment of the disclosure, the bacterial infection comprises an infection caused by a drug-resistant bacterium.

In yet another embodiment of the disclosure, the drug-resistant bacterium is a vancomycin-resistant bacterium or a methicillin-resistant bacterium.

In still another embodiment of the disclosure, the bacterium comprises a vancomycin-resistant *Staphylococcus aureus*, a vancomycin-resistant *Enterococcus faecium* or a methicillin-resistant *Staphylococcus aureus*.

In still another embodiment of the disclosure, the bacterial infection comprises an infection caused by *E. coli*.

The present disclosure also relates to an article comprising:
a composition comprising the compound of any of claims 1-10 or the pharmaceutically acceptable salt of claim 11.

In still another embodiment of the disclosure, the substrate is coated with or impregnated with the composition comprising the compound of any of claims 1-10 or the pharmaceutically acceptable salt of claim 11.

To more clearly and concisely describe and point out the subject matter of the claimed invention, the following definitions are provided for specific terms, which are used in the following description and the appended claims.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

As used herein the term "aliphatic radical" refers to an organic radical having a valence of at least one comprising a linear or branched acyclic or non-aromatic cyclic array of atoms. The non-aromatic cyclic aliphatic radical may comprise one or more noncyclic components. For example, a cyclohexylmethyl group ($C_6H_{11}CH_2$—) is a cycloaliphatic radical which comprises a cyclohexyl ring (the array of atoms which is cyclic but which is not aromatic) and a methylene group (the noncyclic component). The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched acyclic or non-aromatic cyclic array of atoms" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. Again, the prop-1-enyl radical ($CH_3CH=CH$—) is a $C_3$ aliphatic radical comprising an alkenyl group. Examples of non-aromatic cyclic radicals include but are not limited to steroids such as cholesterol and ergosterol. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. —CH$_2$CHBrCH$_2$—), and the like. Aliphatic radicals comprising one or more alkenyl groups may include octadec-9-enyl radical (CH$_3$(CH$_2$)$_7$CH=CH(CH$_2$)$_7$CH$_2$—), which is a C$_{18}$ aliphatic radical comprising single alkenyl group and octadec-9,12-dienyl radical (CH$_3$(CH$_2$)$_4$CH=CHCH$_2$CH=CH(CH$_2$)$_7$CH$_2$—), which is a C$_{18}$ aliphatic radical comprising two alkenyl groups. Further examples of aliphatic radicals include allyl (CH$_2$=CHCH$_2$—), propargyl (CH≡CCH$_2$—), aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e. —CHO), hexyl, hexamethylene, hydroxymethyl (i.e. —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilypropyl (i.e., (CH$_3$O)$_3$SiCH$_2$CH$_2$CH$_2$—), vinyl, vinylidene, and the like. By way of further example, a C$_1$-C$_{10}$ aliphatic radical contains at least one but no more than 10 carbon atoms. A methyl group (i.e., CH$_3$—) is an example of a C$_1$ aliphatic radical. A decyl group (i.e., CH$_3$(CH$_2$)$_9$—) is an example of a C$_{10}$ aliphatic radical.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), and anthraceneyl groups (n=3). The aromatic radical may also include nonaromatic components. For example, benzyl (C$_6$H$_5$CH$_2$—), naphthyl-1-methyl (C$_{10}$H$_7$CH$_2$—), anthracenyl-1-methyl (C$_{14}$H$_9$CH$_2$—) are aromatic radicals, which comprise a phenyl ring, a naphthyl ring, an anthracenyl ring (the aromatic group) respectively and a methylene group (the nonaromatic component). Similarly a tetrahydronaphthyl radical is an aromatic radical comprising an aromatic group (C$_6$H$_3$) fused to a nonaromatic component —(CH$_2$)$_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a C$_7$ aromatic radical comprising a methyl group, the methyl group being a functional group which is an alkyl group. Similarly, the 2-nitrophenyl group is a C$_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC(CF$_3$)$_2$PhO—), 4-chloromethylphen-1-yl, 3-trifluorovinyl-2-thienyl, 3-trichloromethylphen-1-yl (i.e., 3-CCl$_3$Ph-), 4-(3-bromoprop-1-yl)phen-1-yl (i.e., 4-BrCH$_2$CH$_2$CH$_2$Ph-), and the like. Examples of aromatic radical include but are not limited to, tocopherol and tocotrienol. Further examples of aromatic radicals include 4-allyloxyphen-1-oxy, 4-aminophen-1-yl (i.e., 4-H$_2$NPh-), 3-aminocarbonylphen-1-yl (i.e., NH$_2$COPh-), 4-benzoylphen-1-yl, dicyanomethylidenebis(4-phen-1-yloxy) (i.e., —OPhC(CN)$_2$PhO—), 3-methylphen-1-yl, methylenebis(4-phen-1-yloxy) (i.e., —OPhCH$_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh(CH$_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g. methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis(phenyl), and the like. The term "a C$_3$-C$_{10}$ aromatic radical" includes aromatic radicals containing at least three but no more than 10 carbon atoms. The aromatic radical 1-imidazolyl (C$_3$H$_2$N$_2$—) represents a C$_3$ aromatic radical. The benzyl radical (C$_7$H$_7$—) represents a C$_7$ aromatic radical.

The term "hydrophobic" as used herein to describe a compound of the present invention or a substituent thereon, refers to the tendency of the compound or substituent thereon to lack an affinity for, to repel or to fail to absorb water, or to be immiscible in water. The term "hydrophobic" is not meant to exclude compounds or substituents thereon that are not completely immiscible in water.

For the purpose of the present invention, the terms "lipophilic" and "hydrophobic" may be used interchangeably.

The term "pharmaceutically acceptable salt" as used herein, refers to salts of the compounds that are substantially non-toxic to living organisms such that it could be effectively used for the treatment of a subject. For example, the pharmacokinetics and pharmcodynamics properties of a pharmaceutically acceptable salt may be suitable for in-vivo usage. Typical pharmaceutically acceptable salts of the compounds of the subject invention include those salts, which are prepared by reaction of the compounds of the present invention with a pharmaceutically acceptable mineral acid or organic acid. Such salts are classified as acid addition salts.

The term "treatment" as used herein includes any treatment of a condition or disease in a subject and includes: (i) preventing the disease or condition from occurring in a subject which may be predisposed to the disease but has not yet been diagnosed as having it; (ii) inhibiting the disease or condition, i.e. arresting its development; relieving the disease or condition, i.e. causing regression of the condition; or relieving the conditions caused by the disease, i.e. symptoms of the disease.

The term "effective amount" as used herein is a concentration at which an active ingredient optimally performs it intended use. For example, it is an amount that is effective to prevent a disease or condition from occurring in a subject and/or inhibit the disease or condition, i.e. arrest its development; relieve the disease or condition, i.e. cause regression of the condition; or relieve the conditions caused by the disease.

"Drug resistant bacterium" as used herein is a bacterium which is able to survive exposure to at least one drug. In some embodiments the drug resistant bacterium is a bacterium which is able to survive exposure to a single drug or multiple drugs. Examples of drug resistant bacterium include but are not limited to vancomycin resistant bacterium or methicillin resistant bacterium.

A "subject" used herein, refers to a multi-cellular living organism. For example, subject may be an animal that may be a vertebrate or an invertebrate. In some embodiments the subject may be a mammal. In some embodiments the subject may be a human being.

In some embodiments a compound of Formula I is provided:

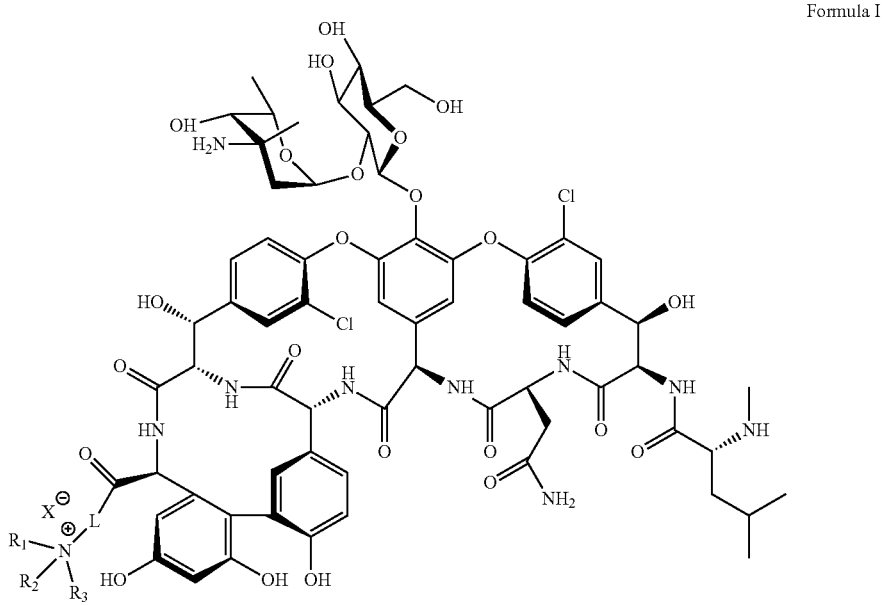

Formula I wherein, L is a $C_2$-$C_{22}$ aliphatic radical or a $C_3$-$C_{22}$ aromatic radical; $R_1$, $R_2$, and $R_3$ are, independently at each occurrence, a $C_1$-$C_{40}$ aliphatic radical or a $C_3$-$C_{40}$ aromatic radical; and at least one of $R_1$, $R_2$, or $R_3$ comprises at least 2 carbon atoms.

L is a linker moiety. In some embodiments, the linker moiety includes at least 2 carbon atoms. In some other embodiments the linker moiety includes more than 2 carbon atoms. For example, linker moiety may be a structural moiety comprising 2 to 22 carbon atoms. The linker may be an aliphatic radical having a structural moiety comprising a noncyclic linear, branched or non-aromatic cyclic array of atoms. In some embodiments, the linker L may be a hydrocarbon moiety, comprising carbon and hydrogen. For example, linker may include structural moiety such as —CH$_2$CH$_2$—, —CH$_2$CH$_2$CH$_2$— and the like. In some embodiments the linker may include one or more alkenyl or alkynyl groups. Example of a linker having an alkenyl group include —CH=CH—CH$_2$—. In some embodiments the linker may include a structural moiety comprising a non-aromatic cyclic array of atoms. For example the linker may include a cyclohexyl group, a cyclopentyl group, and the like. In some other embodiments, linker may have one or more heteroatoms such as nitrogen, sulfur, silicon, selenium and oxygen. For example linker may include a structural moiety such as —NHCH$_2$CH$_2$—, —NHCH$_2$CH$_2$CH$_2$—, —NHCH$_2$CH$_2$OCH$_2$CH$_2$— and the like. In some embodiments, the linker may include an aromatic moiety. For example the linker may include a phenyl group, a pyridyl group, a naphthyl group and the like.

In some embodiments, L may include an aliphatic radical comprising 2 to 8 carbon atoms. For example, L may include —NHCH$_2$CH$_2$—, —NHCH$_2$CH$_2$CH$_2$—, —NHCH$_2$CH$_2$OCH$_2$CH$_2$—, —NHCH$_2$(CH$_2$)$_6$CH$_2$—, and the like.

In some embodiments $R_1$, $R_2$, and $R_3$ includes a structural moiety comprising 1 to 40 carbon atoms. $R_1$, $R_2$, and $R_3$ may be aliphatic radical including noncyclic linear, branched or non-aromatic cyclic array of atoms. For example $R_1$, $R_2$, and $R_3$ may be CH$_3$—, CH$_3$CH$_2$—, CH$_3$(CH$_2$)$_n$— where n is an integer ranging from 2 to 39. In some embodiments $R_1$, $R_2$, and $R_3$ may include one or more alkenyl or alkynyl groups. Examples include but are not limited to, octadec-9-enyl (CH$_3$(CH$_2$)$_7$CH=CH(CH$_2$)$_7$CH$_2$—), which is a $C_{18}$ aliphatic structural moiety comprising single alkenyl group and octadec-9,12-dienyl radical (CH$_3$(CH$_2$)$_4$CH=CHCH$_2$CH=CH(CH$_2$)$_7$CH$_2$—), which is a $C_{18}$ aliphatic radical comprising two alkenyl groups. In some other embodiments, $R_1$, $R_2$, and $R_3$ may have one or more heteroatoms such as nitrogen, sulfur, silicon, selenium and oxygen. In some embodiments $R_1$, $R_2$, and $R_3$ may include a wide range of structural moieties such as haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example $R_1$, $R_2$, or $R_3$ may be:

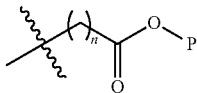

wherein, P is a $C_1$-$C_{24}$ aliphatic saturated radical or a $C_2$-$C_{24}$ aliphatic unsaturated radical, and n is an integer ranging from 1 to 4.

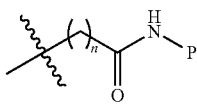

wherein, P is a $C_1$-$C_{24}$ aliphatic saturated radical or a $C_2$-$C_{24}$ aliphatic unsaturated radical, and n is an integer ranging from 1 to 4,

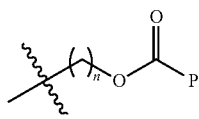

wherein, P is a $C_1$-$C_{24}$ aliphatic saturated radical or a $C_2$-$C_{24}$ aliphatic unsaturated radical, and n is an integer ranging from 1 to 4,

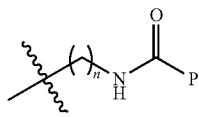

wherein, P is a $C_1$-$C_{24}$ aliphatic saturated radical or a $C_2$-$C_{24}$ aliphatic unsaturated radical, and n is an integer ranging from 1 to 4,

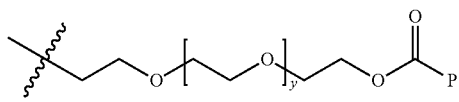

wherein, P is a $C_1$-$C_{24}$ aliphatic saturated radical or a $C_2$-$C_{24}$ aliphatic unsaturated radical, and n is an integer ranging from 0 to 3,

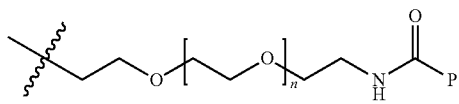

wherein, P is a $C_1$-$C_{24}$ aliphatic saturated radical or a $C_2$-$C_{24}$ aliphatic unsaturated radical, and n is an integer ranging from 0 to 3.

In some embodiments P includes an aliphatic saturated radical comprising 1 to 24 carbon atoms. P may include noncyclic linear, branched or non-aromatic cyclic array of atoms. For example P may be $CH_3$—, $CH_3CH_2$—, or $CH_3(CH_2)_n$— where n is an integer ranging from 2 to 23. In some embodiments P may include aliphatic unsaturated radical comprising 2 to 24 carbon atoms. P may include one or more alkenyl or alkynyl groups. Examples of aliphatic unsaturated radical include but are not limited to $CH_3(CH_2)_7CH=CH(CH_2)_6CH_2$—, which is an aliphatic structural moiety comprising single alkenyl group and $CH_3(CH_2)_4CH=CHCH_2CH=CH(CH_2)_6CH_2$—, which is an aliphatic radical comprising two alkenyl groups.

In some embodiments, $R_1$, $R_2$ and $R_3$ may include non-aromatic cyclic radical having a structural moiety such as steroids (cholesterol, ergosterol etc). For example $R_1$, $R_2$ and $R_3$ may be

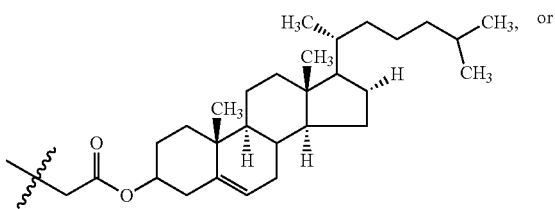

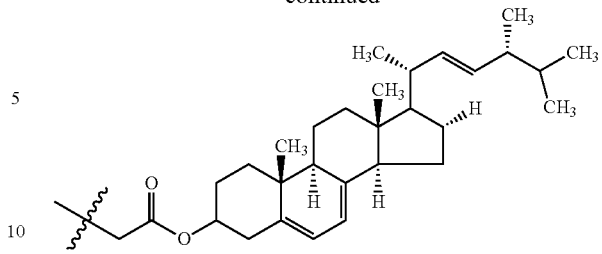

In some embodiments $R_1$, $R_2$, and $R_3$ may include an aromatic radical having an array of atoms having a valence of at least one comprising at least one aromatic group. The aromatic group may include heteroatoms such as nitrogen, sulfur, selenium, silicon and oxygen, or may be composed exclusively of carbon and hydrogen. Examples of aromatic radical include but are not limited to phenyl, pyridyl, furanyl, thienyl, naphthyl, anthryl, phenylene, and biphenyl radicals. The aromatic radical may also include nonaromatic components. For example, benzyl ($C_6H_5CH_2$—), naphthyl-1-methyl ($C_{10}H_7CH_2$—), anthracenyl-1-methyl ($C_{14}H_9CH_2$—) are aromatic radicals, which comprise a phenyl ring, a naphthyl ring, an anthracenyl ring (the aromatic group) respectively and a methylene group (the nonaromatic component). In some embodiments, aromatic radical may include a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is an aromatic radical comprising a methyl group, the methyl group being a functional group which is an alkyl group. Similarly, the 2-nitrophenyl group is an aromatic radical comprising a nitro group. Aromatic radicals may include halogenated aromatic radicals.

Examples of aromatic radical include but are not limited to, tocopherol or tocotrienol. In some embodiments, $R_1$, $R_2$ and $R_3$ may include an aromatic radical having a structural moiety such as α-Tocopherol, β-Tocopherol, γ-Tocopherol, δ-Tocopherol. For example $R_1$, $R_2$ and $R_3$ may be:

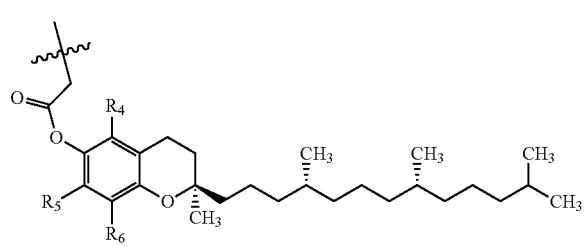

wherein, $R_4=R_5=R_6=$—$CH_3$ or $R_4=R_6=$—$CH_3$ and $R_5=$—H or $R_4=$—H and $R_5=R_6=$—$CH_3$ or $R_4=R_5=$—H, $R_6=$—$CH_3$.

In some embodiments, $R_1$, $R_2$ and $R_3$ may include an aromatic radical having a structural moiety such as α-Tocotrienol, β-Tocotrienol, γ-Tocotrienol, δ-Tocotrienol. For example $R_1$, $R_2$ and $R_3$ may be

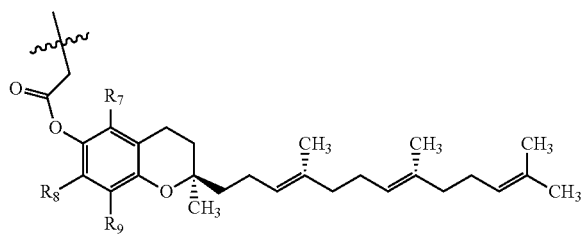

wherein, $R_7=R_8=R_9=$—$CH_3$ or $R_7=R_9=$—$CH_3$ and $R_8=$—H or $R_7=$—H and $R_8=R_9=$—$CH_3$ or $R_7=R_8=$—H and $R_9=$—$CH_3$.

In some embodiments $R_1$, $R_2$ and $R_3$ may be a "hydrophobic moiety" comprising non-cyclic linear, branched or cyclic array of atoms with at least six carbon atoms. In some embodiments the "hydrophobic moiety" may include an aromatic radical. In one aspect of this embodiment said hydrophobic moiety comprises more than 6 and up to 40 carbon atoms. In a second aspect said hydrophobic moiety comprises between 6 and 24 carbon atoms and in a third aspect said hydrophobic moiety comprises between 8 and 14 carbon atoms. In some embodiments said hydrophobic moiety may include one or more heteroatoms such as nitrogen, sulfur, silicon, selenium and oxygen. In one embodiment said hydrophobic moiety may include one or more alkenyl or alkynyl groups. In other embodiments said hydrophobic moiety may include a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. In some embodiments the branching of the main chain of said hydrophobic moiety may comprise small building blocks. Preferred building blocks comprise methyl-, ethyl-, propyl-, isopropyl-, methoxy-, ethoxy-, methoxymethyl-, ethoxymethyl-, methoxyethyl-, ethoxyethyl- and vinyl- or halogen groups or mixtures thereof. Alternatively, said hydrophobic moiety may include sterols, said sterols may further include functional groups.

In the compound of Formula I, $R_1$, $R_2$, and $R_3$ are independently selected from an aliphatic radical or an aromatic radical. In some embodiments $R_1$, $R_2$, and $R_3$ may all be different radicals; for example, $R_1$ may be methyl radical ($CH_3$—), $R_2$ may be ethyl radical ($CH_3CH_2$—) and $R_3$ may be propyl radial ($CH_3CH_2CH_2$—). In some embodiments, $R_1$ and $R_2$ may be a same radical and $R_3$ may be a different radical from $R_1$ and $R_2$; for example $R_1$ and $R_2$ may be a methyl radical ($CH_3$—), and $R_3$ may be ethyl radical ($CH_3CH_2$—). In some embodiments $R_1$ and $R_3$ may be a same radical and $R_2$ may be a different radical from $R_1$ and $R_3$; for example $R_1$ and $R_3$ may be a methyl radical ($CH_3$—), and $R_2$ may be an ethyl radical ($CH_3CH_2$—). In some embodiments $R_2$ and $R_3$ may be a same radical and $R_1$ may be a different radical from $R_2$ and $R_3$; for example $R_2$ and $R_3$ may be a methyl radical ($CH_3$—), and $R_1$ may be an ethyl radical ($CH_3CH_2$—). In some embodiments $R_1$, $R_2$, and $R_3$ may all be a same radical; for example $R_1$, $R_2$, and $R_3$ may be an ethyl radical ($CH_3CH_2$—).

In the compound of Formula I, at least one of $R_1$, $R_2$, or $R_3$ comprises at least 2 carbon atoms. For example in some embodiments, $R_1$ may be a methyl radical ($CH_3$—), $R_2$ may be a methyl radical ($CH_3$—), and $R_3$ may be an ethyl radical ($CH_3CH_2$—).

In some embodiments a compound of Formula II is provided:

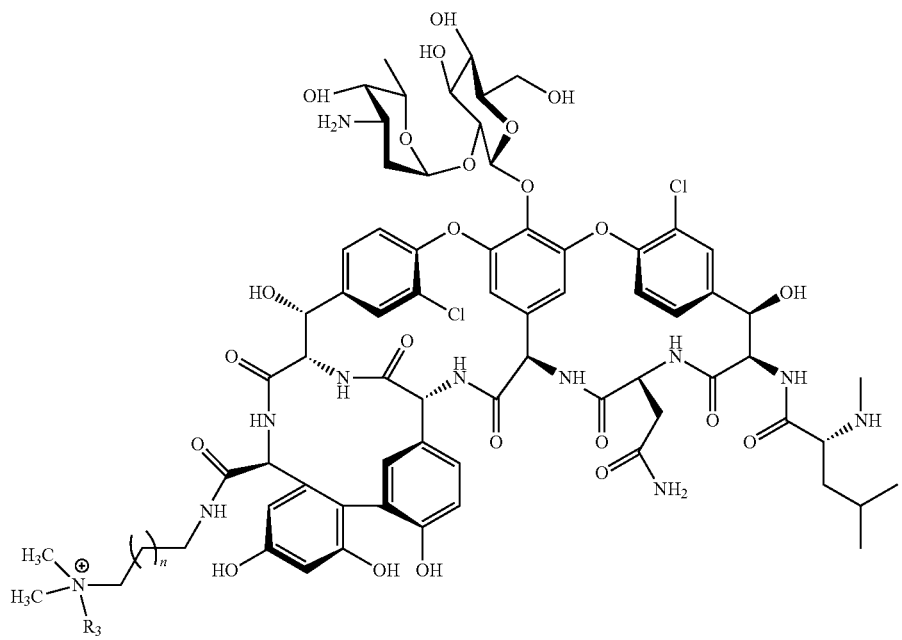

Formula II wherein, $R_3$ is an aliphatic saturated radical represented by formula $C_mH_{2m+1}$, wherein m is an integer ranging from 8 to 14, and wherein n is an integer ranging from 0 to 3.

In some embodiments $R_3$ may include $CH_3(CH_2)_7$—, $CH_3(CH_2)_8$—, $CH_3(CH_2)_9$—, $CH_3(CH_2)_{10}$—, $CH_3(CH_2)_{11}$—, $CH_3(CH_2)_{12}$—, or $CH_3(CH_2)_{13}$—.

In some embodiments, a pharmaceutically acceptable salt of the compounds of the present invention with a pharmaceutically acceptable mineral acid or organic acid include hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, trifluoroacetic acid, salicylic acid, terephthalic acid and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, trifluoroacetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methanesulfonate, propanesulfonate, naphthalene-1-sulfonate, naphthalene-2-sulfonate, mandelate and the like.

In some embodiments, a pharmaceutically acceptable salt of the compounds of the present invention may be with a pharmaceutically acceptable organic acid such as trifluoroacetic acid and the pharmaceutically acceptable salt may be trifluoroacetate.

It should be recognized that the particular counterion (for example X⁻ as shown in formula 1) forming a part of any salt of this invention may not be of a critical nature, so long as the salt as a whole is pharmacologically acceptable and as long as the counterion does not contribute undesired qualities to the salt as a whole.

In some embodiments, the "composition" may be a composition comprising drug along with conventional pharmaceutical carriers. In some other embodiments, the excipients formulated for immediate or sustained release. Other time-release profiles, such as combinations of immediate and sustained release are also possible. As used herein, the term "pharmaceutically carrier and/or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray, or a liquid aerosol or dry powder formulation for inhalation.

Liquid dosage forms for oral administration include pharmaceutically acceptable emulsions, microemulsions, liposome, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, any oil including mono- or diglycerides or fatty acids such as oleic acid can be used in the preparation of injectables.

In order to prolong the effect of a drug, it is often desirable to slow the release of the drug. Slow release of the drug can be accomplished by dissolving or suspending the drug in an oil vehicle. Injectable depot forms can be made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions which are compatible with body tissues. Alternatively, the compounds of this invention can be conjugates covalently, encapsulated, or adsorbed onto carbon nanospheres or nanotubes to form slow release compositions.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes.

The active compounds can also be in micro-encapsulated form with one or more excipients as noted above. The solid dosage forms of tablets, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Alternatively, the compound or the pharmaceutical composition thereof, can also be coated or impregnated into catheters or stents for local drug delivery.

In some embodiments a method of making a lipophilic quarternary ammonium derivative of vancomycin is described. The method comprising activating a carboxylic acid moiety of vancomycin to generate an activated vancomycin; and reacting the activated vancomycin with a primary amine comprising a lipophilic quarternary ammonium moiety.

Lipophilic quarternary ammonium moiety comprises a structural moiety of general formula:

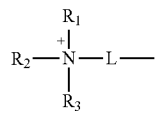

wherein, L is a $C_2$-$C_{22}$ aliphatic radical or a $C_3$-$C_{22}$ aromatic radical; $R_1$, $R_2$, and $R_3$ are, independently at each occurrence, a $C_1$-$C_{40}$ aliphatic radical or a $C_3$-$C_{40}$ aromatic radical; and at least one of $R_1$, $R_2$, or $R_3$ comprises at least 2 carbon atoms.

Examples of lipophilic quarternary ammonium moiety include but are not limited to, $CH_3(CH_2)_7N^+(CH_3)_2CH_2CH_2CH_2NH_2$,
$CH_3(CH_2)_9N^+(CH_3)_2CH_2CH_2CH_2NH_2$,
$CH_3(CH_2)_{11}N^+(CH_3)_2CH_2CH_2CH_2NH_2$,
$CH_3(CH_2)_{13}N^+(CH_3)_2CH_2CH_2CH_2NH_2$,
$CH_3(CH_2)_7CH=CH(CH_2)_7CH_2N^+(CH_3)_2CH_2CH_2CH_2NH_2$,
$CH_3(CH_2)_4CH=CHCH_2CH=CH(CH_2)_7CH_2N^+(CH_3)_2CH_2CH_2CH_2NH_2$,
$CH_3(CH_2)_7OCOCH_2N^+(CH_3)_2CH_2CH_2CH_2NH_2$,
$CH_3(CH_2)_7NHCOCH_2N^+(CH_3)_2CH_2CH_2CH_2NH_2$,
$CH_3(CH_2)_7CH=CH(CH_2)_6COOCH_2CH_2CH_2N^+(CH_3)_2CH_2CH_2CH_2NH_2$, or $CH_3(CH_2)_7CH=CH(CH_2)_6CONHCH_2CH_2CH_2^+(CH_3)_2CH_2CH_2CH_2NH_2$.

In some embodiments, a method of forming an amide at the carboxyl group of vancomycin is described. The method comprises forming an activated ester intermediate of the vancomycin followed by reaction with the lipophilic quarternary ammonium moiety. Other methods of forming amide linkages, known to the ordinarily skilled chemist may be employed as well, subject of course, to suitable protection of other groups in the molecule which might be reactive under the conditions employed to form the amide linkage at the terminal carboxyl group. Thus, for example, the carboxyl group may be activated by reaction with, e.g., O-Benzotriazole-N,N,N',N'-tetramethyl-uronium-hexafluoro-phosphate (HBTU) to form an amine-reactive activated ester intermediate, followed by reaction with lipophilic quarternary ammonium moiety to yield a compound of the present invention which is an amide modification of the terminal carboxyl group. The reaction of the carboxyl group with HBTU and the subsequent reaction with the amine are conducted in a suitable solvent which may be aqueous, organic or a combination of aqueous/organic solvents. Exemplary solvents include, but are not limited to DMF, (dimethylformamide), DMSO (dimethylsulphoxide), methylene chloride, hexanes, methanol and mixtures thereof. Other compounds which activate the terminal carboxyl group in a manner similar to HBTU include, for example, hydroxybenzotriazole (HOBt), 1-ethyl-3-(3-dimethylaminopropyl)carbodiimide hydrochloride (EDC), or dicyclohexylcarbodiimide (DCC). Other protocols for activating a carboxyl group to render it more amenable to reaction with an amine to form a peptide linkage are known to the ordinarily skilled chemist and may be employed to form the amide modification of the terminal carboxyl group.

The compounds of the present invention, or pharmaceutically acceptable salts or compositions thereof can be formulated for any conventional means of delivery, including oral or parenteral delivery for the therapeutic or prophylactic treatment of infectious diseases, preferably bacterial diseases. The bacterial diseases which may be therapeutically or prophylactically treated with the compounds and/or formulations of the present invention include those caused by Gram-positive and/or Gram-negative microorganisms.

The compounds of the present invention may be administered separately or in combination with any other drug or therapeutic agent. Examples of other therapeutic agents and/or drugs that can be administered with the compounds and/or formulations of the present invention include, but are not limited to, beta lactam antibiotics, such as penems, penams, cephems, carbapenems, oxacephems, carbacephems, and monobactams, or other antibiotics such as cycloserine and fosfomycin. The other therapeutic agent need not be an antibiotic.

The compound and/or composition are administered to the subject in a therapeutically effective amount. Thus, the compound of the present invention can be administered to the subject, preferably a human, in an amount ranging from about 0.25 to about 2 grams per day. The compound and/or composition of the present invention can be administered in a single daily dosage or in multiple doses per day. Other periodic treatment protocols may also be adopted. Thus, the treatment protocol may require administration over extended periods of time, e.g., for several days or for from about one to six weeks. The therapeutically effective amounts of the compound of the invention discussed above are merely exemplary. Thus, the amount per administered dose or the total amount administered will depend on such factors as the nature and severity of the infection, the age and general health of the patient, the tolerance of the patient to the compounds and/or formulations of the present invention and the microorganism or microorganisms involved in the infection.

In some embodiments, treatment includes preventing a disease or condition from occurring in a subject which may be predisposed to the disease but has not yet been diagnosed as having it. In some other embodiments, treatment includes inhibiting the disease or condition, i.e. arresting its development; relieving the disease or condition, i.e. causing regression of the condition; or relieving the conditions caused by the disease, i.e. symptoms of the disease.

In the present invention, the desired therapeutic effect would be treatment of a disease condition resulting from gram positive, gram negative, or acid fast bacterial infections. These include but are not limited to diseases such as infective endocarditis, skin infections, meningitis, urinary tract infections, gastrointestinal infections, respiratory tract infections etc caused by pathogenic bacteria such as *Staphylococci, Streptococci, Haemophilus, Moraxalla, Chlamydia, Rickettsiae, Mycoplasm, Legionella, Mycobacterium, Helicobacter, Clostridium, Bacteroides, Propionibacterium acnes, Corynebacterium, Bacillus* or *Enterobactericeae* etc.

In some embodiments, bacterial infections may be caused by drug sensitive bacteria, or drug resistant bacteria. In some other embodiments, infections may caused by drug sensitive bacteria, which later become drug resistant once inside the body of the infected host. In some embodiments, infections may be caused by both drug sensitive bacteria and drug resistant bacteria.

In some embodiments, drug sensitive bacteria may include but are not limited to *Staphylococci, Streptococci, Enterococci, Haemophilus, Moraxalla, Chlamydia, Rickettsiae, Mycoplasm, Legionella, Mycobacterium, Helicobacter, Clostridium, Bacteroides, Propionibacterium acnes, Corynebacterium, Bacillus* or *Enterobactericeae* etc.

In some other embodiments, drug resistant bacteria may include but are not limited to methicillin resistant *S. aureus* (MRSA), vancomycin resistant *S. aureus* (VRSA), vancomycin resistant *E. faecalis*, vancomycin resistant *E. faecium*. In some embodiments, the compounds of the present invention and pharmaceutically acceptable salts thereof show good antibacterial activity against methicillin resistant *S. aureus* (MRSA), vancomycin resistant *S. aureus* (VRSA), vancomycin resistant *E. faecalis* (VRE).

In some embodiments, infection may be caused by Gram-negative bacteria, for example *E. coli*, which is an inherently vancomycin resistant bacteria. In some embodiments, the compounds of the present invention and pharmaceutically acceptable salts thereof show good antibacterial activity against *E. coli*.

In some embodiments, a subject refers to a multi-cellular living organism. For example, subject may be an animal that may be a vertebrate or a inveterbate. In some embodiments the subject may be a mammal. In some embodiments the subject may be a human being.

In some embodiments, an article comprising a composition comprising the compound of the present invention or pharmaceutically acceptable salt thereof, include but are not limited to medical implants, catheters, or stents. For example, the compound of the present invention or pharmaceutically acceptable salt thereof may be coated on or impregnated into the medical implants, catheters, or stents.

EXAMPLES

The following examples provide details concerning the synthesis, properties, activities, and applications of the compounds of the present invention. It should be understood the following is representative only, and that the invention is not limited by the details set forth in these examples.

Materials:

All reagents were purchased from Sigma-Aldrich and SD Fine and used without further purification. Analytical thin layer chromatography (TLC) was performed on TLC plates pre-coated with silica gel 60 $F_{254}$ (250 µm thickness). Visualization was accomplished using UV light and Iodine. Column chromatography was performed on silica gel (60-120 $A^0$ pore size). HPLC analysis was performed on a Liquid chromatograph instrument ($C_{18}$ column, 10 mm diameter, 250 mm length) with UV detector monitoring at 254 nm. Nuclear magnetic resonance spectra were recorded on 400 MHz spectrometer in deuterated solvents. MALDI mass spectra (MALDI-MS) were used to characterize the compounds. Bacterial strains, *S. aureus* MTCC 737 and *E. coli* MTCC 443 purchased from MTCC (Chandigarh, India) and MRSA ATCC 33591, Enterococcal strains were obtained from ATCC (Rockvillei, Md.). VRSA strain (MMC-20) was isolated from Midnapore Medical College and Hospital, Midnapore, West Bengal, India. Tryptic-soy agar media was used for *Staphylococci* and sheep blood agar plates were used for *Enterococci*. Plate Reader was used to measure absorbance. Fluorescence measurements were obtained using a spectrofluorometer. Human RBCs were used for hemolytic assay and HeLa cells were used for cytotoxic studies.

Example: 1

Cationic antibacterial compounds (1-8 and 14) of the instant disclosure were synthesized by coupling carboxylic group of vancomycin with cationic moieties through amide coupling using O-Benzotriazole-N,N,N',N'-tetramethyl-uronium-hexafluoro-phosphate (HBTU) (FIG. 1). To synthesize the cationic moieties (12a-12g), N,N-dimethyl-1,3-propanediamine was protected using Di-t-butylpyrocarbonate then quarternized the tertiary amine group by various alkyl bromide followed by deprotection of primary amine group under acidic conditions (FIG. 2). The steps employed in the method of synthesising cationic moeity represented in FIG. 2 is further elaborated below in Examples 1.1-1.3.

Example 1.1

Synthesis of NH-Boc N,N-dimethyl 1,3 propanediamine (10)

N,N-Dimethyl 1,3 propanediamine (about 3.27 g, about 31.9 mmol) was dissolved in about 1M NaOH solution (about 100 ml) and four equivalents of (Boc)$_2$O (about 27.92 g, about 127 mmol) was added to it. The reaction mixture was stirred vigorously at room temperature (20-35° C.), atmospheric pressure (1 atm) for about 10 h and from the reaction mixture compound 10 was extracted into the organic layer using chloroform. The resultant organic solution was evaporated and dried to afford colourless oily NH-Boc N,N-dimethyl 1,3 propanediamine with about 70% yield. $^1$HNMR (400 MHz, CD$_3$OD) δ/ppm: 3.07-3.04 (t, 2H), 2.4-2.33 (q, 2H), 2.26 (s, 6H), 1.69-1.62 (m, 2H), 1.43 (s, 9H). $^{13}$CNMR (100 MHz, CD$_3$OD) δ/ppm: 157.2, 78.43, 57.32, 45.784, 38.8, 26.2.

Example 1.2: Synthesis of NH-Boc N-alkyl N,N-dimethyl 1,3 propanediamine (11a-11g)

Compound 10 (about 1 g, about 4.92 mmol) was dissolved in dry ethanol (about 10 ml) in a sealed tube and alkyl bromide (about 9.84 mmol) was added to it. The reaction mixture was refluxed for about 48 h. After that the required compounds were purified by column chromatography using Silica gel of mesh size (about 60-120) and using about 10-20% CH$_3$OH/CHCl$_3$ as eluant and the quarternised NH-Boc derivatives, (11a-11g) yield was about 60-65%.

NH-Boc N-ethyl N,N-dimethyl 1,3 propanediamine (11a)

$^1$HNMR (400 MHz, CD$_3$OD) δ/ppm: 3.4-3.33 (t, 2H), 3.25-3.1 (t, 2H), 3.2 (s, 6H), 3.05-3.01 (q, 2H), 1.44 (s, 9H), 1.25-1.10 (t, 3H).

NH-Boc N-butyl N,N-dimethyl 1,3 propanediamine (11b)

$^1$HNMR (400 MHz, CD$_3$OD) δ/ppm: 3.35-3.33 (t, 2H), 3.16-3.13 (t, 2H), 3.12 (s, 6H), 1.97-1.90 (m, 2H), 1.82-1.70 (m, 2H), 1.44 (s, 9H), 1.04-1.00 (t, 3H).

NH-Boc N-octyl N,N-dimethyl 1,3 propanediamine (11c)

$^1$HNMR (400 MHz, CDCl$_3$) δ/ppm: 5.65-5.62 (t, 1H), 3.71-3.67 (t, 2H), 3.44-3.39 (t, 2H), 3.33 (s, 6H), 3.29-3.24 (q, 2H), 2.08-2.01 (m, 2H), 1.73-1.67 (m, 2H), 1.35-1.25 (m, 10H), 1.43 (s, 9H), 0.89-0.86 (t, 3H). $^{13}$CNMR (100 MHz, CDCl$_3$) δ/ppm: 156.2, 64.67, 62.31, 51.31, 31.59, 29.1, 28.98, 28.4, 26.3, 23.5, 22.8, 22.5, 14.01.

NH-Boc N-decyl N,N-dimethyl 1,3 propanediamine (11d)

$^1$HNMR (400 MHz, CDCl$_3$) δ/ppm: 5.67 (bs, 1H), 3.48-3.46 (t, 2H), 3.33-3.29 (t, 2H), 3.16 (s, 6H), 1.9-1.86 (m, 2H), 1.55 (m, 2H), 1.25 (s, 9H), 1.17-1.08 (m, 16H), 0.72-0.68 (t, 3H). $^{13}$CNMR (100 MHz, CDCl$_3$) δ/ppm: 156.18, 78.98, 64.26, 61.92, 51.0, 49.53, 37.25, 31.58, 29.28, 29.13, 29.00, 28.94, 28.18, 26.03, 23.16, 22.53, 13.8.

NH-Boc N-dodecyl N,N-dimethyl 1,3 propanediamine (11e)

$^1$HNMR (400 MHz, CDCl$_3$) δ/ppm: 5.67 (bs, 1H), 3.48-3.46 (t, 2H), 3.33-3.29 (t, 2H), 3.16 (s, 6H), 1.9-1.86 (m, 2H), 1.55 (m, 2H), 1.25 (s, 9H), 1.17-1.08 (m, 18H), 0.72-0.68 (t, 3H). $^{13}$CNMR (100 MHz, CDCl$_3$) δ/ppm: 156.18, 78.98, 64.26, 61.92, 51.0, 49.53, 37.25, 31.58, 29.28, 29.18, 29.13, 29.00, 28.94, 28.18, 26.03, 23.16, 22.53, 22.36, 13.8.

NH-Boc N-tetradecyl N,N-dimethyl 1,3 propanediamine (11f)

$^1$HNMR (400 MHz, CDCl$_3$) δ/ppm: 5.68 (bs, 1H), 3.68-3.64 (t, 2H), 3.43-3.39 (t, 2H), 3.33 (s, 6H), 3.29-3.23 (m, 2H), 2.07-2.00 (m, 2H), 1.71-1.7 (m, 2H), 1.42 (s, 9H), 1.33-1.23 (m, 22H), 0.88-0.84 (t, 3H). $^{13}$CNMR (100 MHz, CDCl$_3$) δ/ppm: 156.21, 79.5, 64.57, 62.25, 51.34, 37.52, 31.89, 29.64, 29.61, 29.55, 29.44, 29.36, 29.32, 29.18, 28.41, 26.28, 23.46, 22.77, 22.65, 14.08.

NH-Boc N-octadecyl N,N-dimethyl 1,3 propanediamine (11g)

$^1$HNMR (400 MHz, CDCl$_3$) δ/ppm: 5.61-5.59 (t, 1H), 3.72-3.68 (t, 2H), 3.44-3.40 (t, 2H), 3.34 (s, 6H), 3.3-3.25 (q, 2H), 2.09-2.02 (m, 2H), 1.81-1.67 (m, 2H), 1.43 (s, 9H), 1.34-1.25 (m, 30H), 0.89-0.86 (t, 3H). $^{13}$CNMR (100 MHz, CDCl$_3$) δ/ppm: 156.1, 79.57, 64.65, 62.3, 51.28, 37.57, 31.9, 29.68, 29.66, 29.63, 29.56, 29.44, 29.36, 29.33, 29.18, 28.4, 26.28, 23.47, 22.78, 22.66, 14.08.

Example 1.3: Synthesis of N-alkyl N,N-dimethyl 1,3 propanediamine hydrochloride (12a-12g)

Quarternised NH-Boc compounds 11 (about 1 g) were dissolved in about 5 ml of MeOH and about 2 ml of about 37% HCl. The reaction mixture was stirred at room temperature for about 5 h and dried in vacuum to afford N-alkyl N,N-dimethyl 1,3 propanediamine derivatives 12a-12g] in quantitative yield as hydrochloride salts.

N-ethyl N,N-dimethyl 1,3 propanediamine hydrochloride (12a)

$^1$HNMR (400 MHz, D$_2$O) δ/ppm: 3.5-3.45 (m, 6H), 3.15-3.13 (m, 2H), 3.13 (s, 6H), 3.09-3.05 (t, 3H). $^{13}$CNMR (100 MHz, D$_2$O) δ/ppm: 61.56, 50.9, 37.8, 28.71, 22.2, 8.5. MALDI-MS: m/z 130.99 (observed); 131.25 (calculated for M$^+$).

N-butyl N,N-dimethyl 1,3 propanediamine hydrochloride (12b)

$^1$HNMR (400 MHz, CD$_3$OD) δ/ppm: 3.54-3.49 (m, 2H), 3.43-3.38 (m, 2H), 3.17 (s, 6H), 3.11-3.0 (t, 2H), 1.48-1.39 (m, 2H), 1.05-1.01 (t, 3H). $^{13}$CNMR (100 MHz, CD$_3$OD) δ/ppm: 65.8, 61.9, 51.46, 51.42, 37.67, 25.41, 22.07, 20.05, 13.8. MALDI-MS: m/z 160.31 (observed); 159.06 (calculated for M$^+$).

N-octyl N,N-dimethyl 1,3 propanediamine hydrochloride (12c)

$^1$HNMR (400 MHz, CD$_3$OD) δ/ppm: 3.61-3.56 (q, 2H), 3.54-3.48 (t, 2H), 3.42-3.38 (t, 2H), 3.18 (s, 6H), 3.3-3.1 (t, 2H), 2.27-2.21 (m, 2H), 1.85-1.8 (m, 2H), 1.39-1.31 (m, 10H), 0.91-0.88 (t, 3H).
$^{13}$CNMR (100 MHz, CD$_3$OD) δ/ppm: 66.1, 62.0, 61.9, 51.4, 45.66, 37.7, 30.2, 27.28, 23.54, 23.52, 22.06, 14.35. MALDI-MS: m/z 216.23 (observed); 216.41 (calculated for M$^+$).

N-decyl N,N-dimethyl 1,3 propanediamine hydrochloride (12d)

$^1$HNMR (400 MHz, CD$_3$OD) δ/ppm: 3.48-3.44 (t, 3H), 3.37-3.34 (m, 2H), 3.14 (s, 6H), 3.07-3.04 (t, 2H), 2.14-2.2 (m, 2H), 1.83-1.78 (m, 2H), 1.4-1.29 (m, 16H), 0.91-0.88 (t, 3H). $^{13}$CNMR (100 MHz, CD$_3$OD) δ/ppm: 66.15, 61.99, 51.36, 37.71, 33.01, 30.68, 30.59, 30.54, 30.4, 30.23, 27.39, 23.60, 14.36. MALDI-MS: m/z 244.4324 (observed); 244.552 (calculated for M$^+$).

N-dodecyl N,N-dimethyl 1,3 propanediamine hydrochloride (12e)

$^1$HNMR (400 MHz, CD$_3$OD) δ/ppm: 3.48-3.44 (t, 3H), 3.37-3.34 (m, 2H), 3.14 (s, 6H), 3.07-3.04 (t, 2H), 2.14-2.2 (m, 2H), 1.83-1.78 (m, 2H), 1.4-1.29 (m, 18H), 0.91-0.88 (t, 3H). $^{13}$CNMR (100 MHz, CD$_3$OD) δ/ppm: 66.15, 61.99, 51.36, 37.71, 33.01, 30.68, 30.59, 30.54, 30.4, 30.23, 27.39, 23.67, 23.60, 22.17, 14.36. MALDI-MS: m/z 272.43 (observed); 272.52 (calculated for M$^+$).

N-tetradecyl N,N-dimethyl 1,3 propanediamine hydrochloride (12f)

$^1$HNMR (400 MHz, CD$_3$OD) δ/ppm: 3.51-3.45 (t, 2H), 3.4-3.35 (m, 2H), 3.15 (s, 6H), 3.09-3.05 (t, 2H), 2.22-2.14 (m, 2H), 1.84-1.78 (m, 2H), 1.4-1.28 (m, 22H), 0.91-0.88 (t, 3H).
$^{13}$CNMR (100 MHz, CD$_3$OD) δ/ppm: 66.17, 62.02, 51.42, 49.83, 37.83, 37.74, 33.0, 30.72, 30.68, 30.67, 30.59, 30.54, 30.4, 30.22, 27.38, 23.66, 23.62, 22.16, 14.39. MALDI-MS: m/z 300.89 (observed); 300.58 (calculated for M$^+$).

N-octadecyl N,N-dimethyl 1,3 propanediamine hydrochloride (12g)

$^1$HNMR (400 MHz, CD$_3$OD) δ/ppm: 3.51-3.46 (t, 2H), 3.4-3.36 (m, 2H), 3.15 (s, 6H), 3.09-3.05 (t, 2H), 2.2-2.16 (m, 2H), 1.84-1.78 (m, 2H), 1.41-1.28 (m, 30H), 0.91-0.88 (t, 3H).
$^{13}$CNMR (100 MHz, CD$_3$OD) δ/ppm: 66.17, 62.02, 51.41, 37.74, 33.03, 30.74, 30.71, 30.62, 30.57, 30.42, 30.24, 27.4, 23.69, 23.63, 22.18, 14.41. MALDI-MS: m/z 356.53 (observed); 356.68 (calculated for M$^+$).

Example: 2

The steps employed in the method of synthesising cationic moeity (14) represented in FIG. 3 is further elaborated below in Examples 2.1-2.2.

Example 2.1: Synthesis of N-Acetyl N,N dimethyl 1,3 propanediamine (13)

A mixture of N,N dimethyl 1,3 propanediamine 9 (about 4.86 g, about 52.8 mmol) and acetic anhydride (about 19.5 g, about 190.9 mmol) was stirred at room temperature for about 1 h after which unreacted acetic anhydride was removed by using high vacuum pump at room temperature. The acetyl product was neutralized, with about 1N sodium hydroxide solution added dropwise till the pH of the solution becomes neutral (pH 7.0), and extracted into chloroform (about 50 ml). The chloroform was removed to yield 13 with about 79% yield. $^1$HNMR (400 MHz, CDCl$_3$) δ/ppm: 6.5 (bs, 1H), 3.33-3.29 (q, 2H), 2.79-2.76 (t, 3H), 2.52 (s, 6H), 2.01 (s, 3H), 1.89-1.82 (m, 2H). $^{13}$CNMR (100 MHz, CDCl$_3$) δ/ppm: 171.1, 55.37, 43.31, 36.95, 24.99, 23.05, 22.56.

Example 2.2: Synthesis of N'-Acetyl N-tetradecyl N,N dimethyl 1,3 propanediamine (14)

A mixture of 13 (about 0.95 g, about 6.56 mmol) and bromotetradecane (about 3.63 g, about 13.13 mmol) were dissolved in 15 ml of dry acetone. Potassium carbonate (about 1.81 g, about 13.15 mmol) was added to the reaction mixture and the reaction mixture was refluxed for about 48 h. Then the solution was filtered to remove potassium carbonate after which the compound was purified by silica gel (about 60-120 mesh size) column chromatography using about 15% of CH$_3$OH: CHCl$_3$ as eluant, to give about 40% yield. $^1$HNMR (400 MHz, CDCl$_3$) δ/ppm: 7.9 (bs, 1H), 3.85 (t, 2H), 3.38 (t, 2H), 3.33 (m, 2H), 3.2 (s, 6H), 2.08 (s, 3H), 1.7 (m, 2H), 1.35-1.25 (m, 22H), 0.88 (t, 3H). $^{13}$CNMR (100 MHz, CDCl$_3$) δ/ppm: 171.7, 64.9, 63, 51.08, 36.11, 31.9, 29.65, 26.29, 22.6, 14.1.

Example: 3

Synthesis of Cationic Antibacterial Compounds (1-8)

Vancomycin hydrochloride (100 mg, 67 μmol) was dissolved in 1:1 mixture of dry dimethyl formamide (1 mL) dry dimethyl sulfoxide (1 mL). To this two equivalents of compounds bearing primary amine group (N,N-Dimethyl 1,3 propanediamine (9), N-alkyl N,N-dimethyl 1,3 propanediamine hydrochloride (12a-12g)) in 1 mL of dry dimethylformamide was added. The reaction mixture was cooled to 0° C., and 0.22 mL (1.5 equivalents) of 0.45 M HBTU solution in DMF was added followed by 58 μL (5.0 equivalents) of diisopropylethylamine (DIPEA). The reaction mixture was then allowed to warm to room temperature and stirred for 8-12 h. The product was purified by preparative reversed-phase HPLC using 0.1% trifluoro acetic acid in H$_2$O/acetonitrile mixture and then lyophilized to afford tris-(trifluoroacetate) salts of final compounds (50-55 μmol, 75-80%).

The cationic antibacterial compounds were purified and characterized by $^1$H-NMR and MALDI-MS (Table 1). The purification was done by preparative reverse phase HPLC using 0.1% Trifluoro acetic acid (TFA) in water/acetonitrile (0-100%) as mobile phase. C$_{18}$ column (10 mm diameter, 250 mm length) and UV detector (at 270 nm wave length) were used. The collected fractions, from HPLC were frozen by liquid N$_2$ and lyophilized in freeze dryer.

TABLE 1

Characterization of Cationic Antibacterial Compounds

| Compound | Retention Time (HPLC) [minutes] | Molecular weight (Cal) [daltons] [M$^+$] | Molecular weight (Obs by MALDI-MS) [daltons] [M$^+$] |
|---|---|---|---|
| Control (Vancomycin) | 7.934 | 1449.3 | 1450.23 |
| 1 | 7.723 | 1533.518 | 1534.56 |
| 2 | 8.448 | 1561.479 | 1561.634 |
| 3 | 8.821 | 1589.532 | 1589.646 |
| 4 | 10.584 | 1645.639 | 1645.734 |
| 5 | 11.521 | 1673.695 | 1673.031 |
| 6 | 12.521 | 1701.745 | 1702.031 |
| 7 | 14.05 | 1730.238 | 1729.908 |
| 8 | 16.11 | 1786.638 | 1786.529 |

Example: 4

In-Vitro Antibacterial Activity

Minimum Inhibitory Concentration (MIC) and Minimum Bactericidal Concentration (MBC):

All cationic antibacterial compounds and control (vancomycin) were assayed in a micro-dilution broth format. Stock solutions were made by serially diluting the compounds using autoclaved Millipore water or broth media. The antibacterial activity of the compounds was determined against Methicillin sensitive *S. aureus* (MSSA), Methicillin resistant *S. aureus* (MRSA), vancomycin sensitive *Enterococcus faecium* (VSE), vancomycin resistant *Enterococcus faecium* (VRE), and *E. coli*. Bacteria, to be tested, were grown for about 10 h in the suitable media, MSSA and MRSA were grown in Yeast-dextrose broth (about 1 g of beef extract, about 2 g of yeast extract, about 5 g of peptone and about 5 g of NaCl in about 1000 mL of sterile distilled water (pH-7)). For solid media, about 5% agar was used along with above mentioned composition. *E. coli* was cultured in Luria Bertani broth (about 10 g of tryptone, about 5 g of yeast extract, and about 10 g of NaCl in 1000 mL of sterile distilled water, pH -7). VSE and VRE were cultured in Brain Heart Infusion broth (Himedia). The bacterial samples were freeze dried and stored at about −80° C. About 5 μl of these stocks were added to about 3 ml of the nutrient broth and the culture was grown for about 6 h at about 37° C. prior to the experiments. This 6 h grown culture gives about 10$^9$ cfu/mL for MSSA and MRSA, while it was about 10$^8$ cfu/mL for *E. coli*, 10$^9$ cfu/mL for both VSE and VRE and this was determined by spread plating method. The 6 h grown culture was diluted to give effective cell concentration of about 10$^5$ cfu/mL which was then used for determining MIC.

Compounds were serially diluted, in sterile water (2 fold dilution is employed) in a way that the working concentration was about 10 μM for MSSA MRSA, and VSE while for VRE and *E. coli* it was about 100 μM. About 50 μL of these serial dilutions were added to the wells of 96 well plate followed by the addition of about 150 μL of bacterial solution. The plates were then incubated at about 37° C., 150 rpm in the incubator and O.D at 600 nm was recorded at an interval of about 10 h and about 24 h using TECAN (Infinite series, M200 pro) Plate Reader. Each concentration had triplicate values and the whole experiment was done at least twice and the MIC value was determined by taking the average of triplicate O. D. values for each concentration and plotting it against concentration. The data was then subjected to sigmoidal fitting. From the curve the MIC value was determined, as the point in the curve where the O.D. was similar to that of control having no bacteria.

For vancomycin resistant *staphylococcus aureus* (VRSA; clinical isolate MMC-20), the MIC of compounds was determined by broth dilution method using Mueller-Hinton broth (MHB), as recommended by the National Committee for Clinical Laboratory Standards. About 5×10$^4$ bacterial cells in MHB culture were treated with different concentrations of compounds, and shaken for 16 h at 37° C. The minimum concentration at which there was no visible turbidity was taken as the MIC of that compound.

MBC values were determined by plating about 50 μl of the solution and later counting the colonies after their development.

The antibacterial activities of compounds against *Staphylococci* (MSSA, MRSA and VRSA) and *Enterococci* (VSE, VRE) were summarized in Table 2. In case of wild type bacterial strains MSSA, the MIC varied from 0.31 to 5.03 μM while for VSE it was 0.12 to 0.63 μM. When tested against pathogenic MRSA and VRSA, these compounds exhibited MIC in the range of 0.31 to 2.42 μM and 0.24 to 2.1 μM respectively. Both the compounds (4 and 5) showed MIC of 0.31 μM against MRSA implying 2 fold more activity than control. Interestingly, the activities of the compounds 4 and 5 against VRSA were >358 fold higher than control with MIC values of 0.25 and 0.24 μM respectively (Table 2). Considering VRE, the MIC fell in the range of 0.7 to >100 μM.

TABLE 2

Antibacterial activities of cationic antibacterial compounds

| | MIC (μM) | | | | |
|---|---|---|---|---|---|
| Compound | MSSA$^a$ | MRSA$^b$ | VRSA$^c$ | VSE$^d$ | VRE$^e$ |
| Vancomycin | 0.63 | 0.63 | >86 | 0.6 | >100 |
| 1 | 0.62 | 0.61 | 0.53 | 0.63 | >100 |
| 2 | 0.39 | 2.42 | 2.1 | 0.45 | >100 |
| 3 | 0.37 | 0.6 | 2.0 | 0.31 | >100 |
| 4 | 0.31 | 0.31 | 0.25 | 0.15 | 12.5 |
| 5 | 0.31 | 0.31 | 0.24 | 0.2 | N.D$^f$ |
| 6 | 0.62 | 0.62 | N.D$^f$ | 0.16 | 6.3 |
| 7 | 1.25 | 0.65 | 1.9 | 0.12 | 0.7 |
| 8 | 5.03 | N.D$^f$ | N.D$^f$ | N.D$^f$ | 1.9 |

$^a$Methicillin sensitive *S. aureus* (MTCC 737).
$^b$Methicillin resistant *S. aureus* (ATCC 33591).
$^c$Vancomycin restant *S. aureus* (Clinical isolate, MMC-20, VanA & VanB).
$^d$Vancomycin sensitive *E. faecium* (ATCC 19634).
$^e$Vancomycin resistant *E. faecium* (VanA, ATCC 51559).
$^f$Not determined.

MBC of control against MSSA was found to be about 2.5 μM whereas for other compounds MBC varied from 0.62-10 μM (Table 3). MBC value for control and compound 4 against MRSA was found to be 2.5 and 0.62 μM respectively (Table 4).

TABLE 3

Antibacterial activities of cationic antibacterial compounds against MSSA.

| Compound | MBC (µM) |
| --- | --- |
| Control | 2.5 |
| 1 | 1.25 |
| 2 | 0.62 |
| 3 | 0.62 |
| 4 | 0.62 |
| 6 | 1.25 |
| 7 | 2.5 |
| 8 | 10 |

TABLE 4

Antibacterial activities of compound 4 and control against MRSA.

| Compound | MBC (µM) |
| --- | --- |
| Control | 2.5 |
| 4 | 0.62 |

The MIC of compounds and control against *E. coli* was found to be 4 to >100 µM and 80-100 µM respectively, whereas the MBC was 12.5 to >100 µM for compounds and >100 µM for control (Table 5).

TABLE 5

Antibacterial activities of cationic antibacterial compounds against *E. coli*.

| Compound | MIC (µM) | MBC (µM) |
| --- | --- | --- |
| Control | 80-100 | >100 |
| 1 | 50 | 50 |
| 2 | 50 | 50 |
| 3 | 25 | 25 |
| 4 | 12.4 | 25 |
| 7 | 5 | 12.5 |
| 8 | >100 | >100 |
| 14 | >100 | >100 |

Example: 5

Time-Kill Assay

The bactericidal activity was assessed by the kinetics or the rate at which it affects the killing action of the compound. Briefly MRSA grown in Yeast-Dextrose broth. A starting inoculum of $1.6 \times 10^8$ CFU/ml was used as initial bacterial colony count. control and compound 4 having final concentrations of 1×MIC, 6×MIC, and 12×MIC were inoculated with MRSA suspensions having starting inocula of $1.6 \times 10^8$ CFU/ml. Bacterial suspension containing specified concentrations of the compound along with negative control (which contains only 0.9% Saline) was incubated at 37° C. with shaking. Aliquots (20 µl) were removed from the cultures at 0, 1, 2 and 3 h and were serially diluted 10-fold in 0.9% saline and plated onto sterile Yeast-Dextrose agar medium. The number of viable cells was determined by plating the 10-fold serial dilution of each sample onto Yeast-dextrose agar medium. Plates were then incubated for 24 h at 37° C., CFU was counted and the total bacterial $\log_{10}$ CFU/ml was determined.

Vancomycin showed relatively slow killing or bacteriostatic effect and did not appear to be dose dependent, whereas killing by compound 4 was rapid and the rate of killing increased with the concentration, where we found 4- to 5-$\log_{10}$-CFU/ml reduction at 3 h for the concentration 12×MIC. (FIG. 4)

Example: 6

Outer Membrane Permeabilization Assay:

The outer membrane permeabilization activity of compound 7 was determined by fluorescence spectroscopic study using NPN (N-phenylnapthylamine) as a probe. Midlog phase *E. coli* cells were harvested (4000 rpm, about 4° C., about 10 min), washed, and resuspended in 5 mM glucose/5 mM HEPES buffer pH 7.2. Then about 10 µL of about 1.875 mM concentration of control and compound 7 in water was added to a cuvette containing about 1.5 mL of cells, followed by addition of about 30 µL of NPN from about 500 µM stock in acetone (the final concentration of NPN is about 10 µM). After immediate addition of NPN the fluorescence was recorded using the excitation wavelength at about 350 nm (slit width: about 10 nm) and emission wavelength at about 420 nm (slit width: about 10 nm). The uptake of NPN as a measure of outer membrane permeabilization was monitored by the increase in fluorescence of NPN for about 10 min using Spectrophtometer. Only Bacteria was used for negative control (FIG. 5).

NPN dye has little or no fluorescence in water but once it reaches the hydrophobic environment, its fluorescence increases. When compound 7 was incubated with bacteria and NPN, a dramatic increase in fluorescence intensity was observed, whereas negligible increase of fluorescence intensity was observed with control (FIG. 5). This in turn confirms the disruption of the outer membrane of *E. coli* by the compound 7.

Cytoplasmic Membrane Depolarization Assay:

Midlog phase bacterial cells were harvested, washed with about 5 mM HEPES and about 5 mM glucose and resuspended in about 5 mM glucose, about 5 mM HEPES buffer and about 100 mM KCl solution in 1:1:1 ratio (about $10^8$ cfu/ml). Measurements were made in a cuvette containing about 2 ml of bacterial suspension and about 2 µM diSC$_3$(5). The fluorescence of the dye was monitored for about 10 min (MSSA) to about 20 min (*E. coli*) at R.T. spectrofluorometer at excitation wavelength of about 622 nm and emission wavelength of about 670 nm. Dye uptake, and resultant self quenching, was modulated by the membrane potential. After reaching the maximum uptake of the dye by bacteria, which was indicated by a minimum in dye fluorescence, (after about 10 min for *S. aureus* and about 20 min for *E. coli*) compounds (4 and 7) and control were added to the cells, and the decrease in potential was monitored by the increase in fluorescence for further about 10 min.

The results (FIG. 6) demonstrate that compounds 4 and 7 dissipated the membrane potential in both concentration and time dependent manner. The compounds caused significant and rapid (within 15 min) membrane depolarization of MSSA at a concentration of 2.5 µM, while control remained ineffective even at a concentration as high as 40 µM (FIG. 6). Similar results were obtained against *E. coli* (FIG. 7).

Inner Membrane Permeabilization Assay:

Midlog phase (grown for about 6 h) *E. coli* and MSSA cells were harvested (about 4000 rpm, about 4° C., about 10 min), washed, and resuspended in PBS buffer of about pH 7.2. Then compounds (4 and 7) and control were added (about 2.5 µM for MSSA and about 10.0 µM for *E. coli* to a cuvette containing about 2.0 mL of cells and about 10 µM propidium iodide (PI). Excitation wavelength: 535 nm (slit width: 10 nm); emission wavelength: 617 nm (slit width: 10 nm). The uptake of PI was measured by the increase in fluorescence of PI for about 10 min as a measure of inner membrane permeabilization.

Unlike control, which did not cause membrane permeability even at the highest concentration of 40 µM tested against MSSA (FIG. 8), compounds 4 and 7 showed strong ability to permeabilize the cytoplasmic membrane (FIG. 8). Similar results were observed against *E. coli* (FIG. 9).

Example: 7

Toxicity

Hemolytic Assay:

Fresh human blood was collected under aseptic conditions in heparinised vacutainers. vancomycin derivatives are serially diluted, in sterile water (about 2 fold dilution is employed) in a way that the working concentration is about 100 µM. Heparinised blood was centrifuged down at about 3500 rpm for about 5 min in order to separate Red Blood Cells and blood plasma. RBC's are then washed couple of times with PBS pH-7.4 and suspended in PBS such that the final concentration of RBC was about 5 vol %. About 150 µL of this is mixed with about 50 µL of serially diluted compound in 96 well plate. The plate was then incubated at about 37° C. for about one hour. Later, the plate was centrifuged down at about 3500 rpm for about 5 min. The lysed RBC releases haemoglobin which was present in the supernatant. The supernatant thus was pipetted out into another fresh 96 well plate and the absorbance was measured at about 540 nm.

Percentage of hemolysis was determined as $(A-A_0)/(A_{total}-A_0) \times 100$, where A is the absorbance of the test well, $A_0$ the absorbance of solution without compound, and $A_{total}$ the absorbance of 100% hemolysis wells (with Triton X-100), all at 540 nm.

Cytotoxicity Assay:

Cytotoxity of compounds 4 and 7 was determined against HeLa cell line following well known MTT assay. Cells were grown in DMEM at about 37° C. in a humidified-air atmosphere (about 5% $CO_2$/95% air) in DMEM complete medium, supplemented with about 10% heat inactivated Fetal Bovine Serum and about 100 units/mL penicillin G, about 100 g/mL streptomycin. Cells were seeded into 96 well plate and kept under the above mentioned conditions till they attained about 80% confluency. Compounds were serially diluted, in sterile water (2 fold dilution is employed) in a way that the working concentration was 100 µM. 50 µL of these dilutions were added to the cells and the volume was made up to 200 µL using DMEM medium. Cells were kept under observation for about 24 h. Later the medium was removed, cells were washed thoroughly with PBS and about 100 µL of MTT solution (about 5 mg/mL) was added to the wells. After about 3 h the MTT was removed, cells were lysed using DMSO and the plate was read at about 570 nm. One containing no compound (untreated cell) and other with about 10 vol % Triton-X 100 solution were also used. Percentage of cell survival was calculated using the formula:

$(A_{treated\ cells}-A_{triton-X\ cells})/(A_{untreated\ cell}-A_{triton-X\ cells}) \times 100$ A plot of % of survival against concentration of compound was plotted using Origin Pro software.

Compounds 4 and 7 showed no significant toxicity against either of the cell types (E.C$_{50}$>about 100 µM for control, 4 and 7. This shows that the newly synthesized compounds 4 and 7 have preferential toxicity against bacterial cells over mammalian cells (Table 6).

TABLE 6

Toxicity of compounds (4 and 7) and control.

| Compound | EC$_{50}$ (µM) | |
|---|---|---|
| | RCB[a] | HeLa[b] |
| Control | >100 | >100 |
| 4 | >100 | >100 |
| 7 | >100 | >100 |

[a]Human Red Blood Cells (RBC).
[b]HeLa cells (cervical cancer cells).

Example: 8

In-Vivo Antibacterial Activity

Mouse Neutropenic Thigh Infection Model:

About six-week-old, specific-pathogen-free female CD-1 mice (weight, about 23 g to about 25 g) were obtained from Animal facility (JNCASR, Bangalore). The mice were rendered neutropenic (about 100 neutrophils/ml) by injecting two doses of cyclophosphamide intraperitoneally about 4 days (about 150 mg/kg) and about 1 day (about 100 mg/kg) before the infection experiment. About 50 µl of ~$10^6$ CFU/ml concentration of the bacterial inoculum (MRSA) was injected into the thigh. About one hour after inoculation, animals were treated i.v. twice with about 12 h intervals with saline, at about 6.45 µmols concentration of vancomycin (about 10 mg/Kg) and compound 4. At about 24 h post first treatment, cohorts of animals were euthanized (using ether) and the thighs were collected aseptically. The thigh was weighed (about 0.7 g to about 0.9 g range) and placed into about 10 ml of sterile saline and homogenized. The dilutions of the homogenate were plated onto agar plates, which were incubated overnight at about 37° C. The bacterial titer was expressed as $\log_{10}$ CFU/gram of thigh weight.

The in-vivo experiment showed about 15-fold more activity for derivative 4 compared to control against MRSA (FIG. 10). This result also suggests that compound 4 showed no in-vivo toxicity at a total concentration of about 25 mg/kg.

We claim:
1. A compound of formula I:

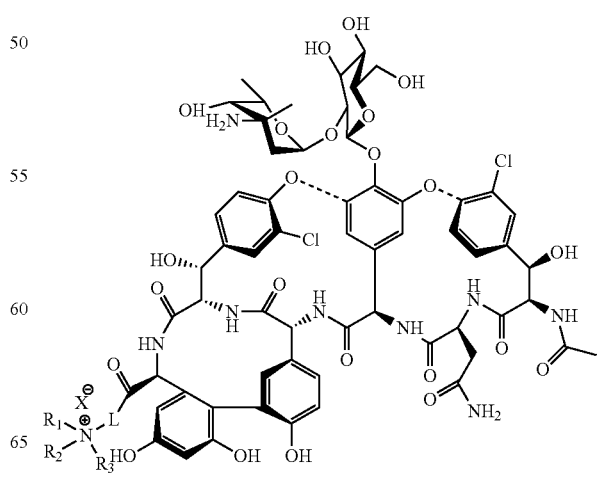

-continued

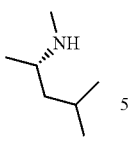

or a pharmaceutically acceptable salt thereof,
wherein,
L is a $C_2$-$C_{22}$ aliphatic radical or a $C_3$-$C_{22}$ aromatic radical linked by an amide bond to a carboxylic group;
$R_1$, $R_2$ and $R_3$ are, independently at each occurrence, a $C_1$-$C_{40}$ aliphatic radical or a $C_3$-$C_{40}$ aromatic radical;
at least one of $R_1$, $R_2$, or $R_3$ comprises at least 5 carbon atoms,
wherein when only one of $R_1$, $R_2$, or $R_3$ is $C_{10}H_{21}$ and L is a saturated $C_3$ aliphatic radical, the remaining two of $R_1$, $R_2$, or $R_3$ are not both methyl groups; and
wherein the compound or pharmaceutically acceptable salt thereof has antibacterial activity.

2. The compound of claim 1, wherein L is a $C_2$-$C_8$ aliphatic radical.

3. The compound of claim 1, wherein $R_3$ is a saturated alkyl radical or an unsaturated alkyl radical.

4. The compound of claim 1, wherein at least one of $R_1$, $R_2$, or $R_3$ comprises a structural moiety selected from the group consisting of:

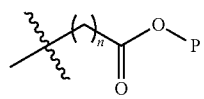

wherein, P is a $C_1$-$C_{24}$ aliphatic saturated radical or a $C_2$-$C_{24}$ aliphatic unsaturated radical, and n is an integer ranging from 1 to 4,

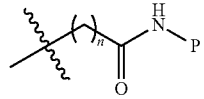

wherein, P is a $C_1$-$C_{24}$ aliphatic saturated radical or a $C_2$-$C_{24}$ aliphatic unsaturated radical, and n is an integer ranging from 1 to 4,

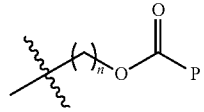

wherein, P is a $C_1$-$C_{24}$ aliphatic saturated radical or a $C_2$-$C_{24}$ aliphatic unsaturated radical, and n is an integer ranging from 1 to 4,

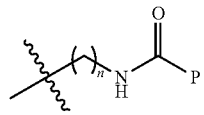

wherein, P is a $C_1$-$C_{24}$ aliphatic saturated radical or a $C_2$-$C_{24}$ aliphatic unsaturated radical, and n is an integer ranging from 1 to 4,

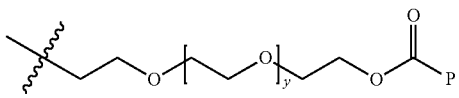

wherein, P is a $C_1$-$C_{24}$ aliphatic saturated radical or a $C_2$-$C_{24}$ aliphatic unsaturated radical, and y is an integer ranging from 0 to 3,

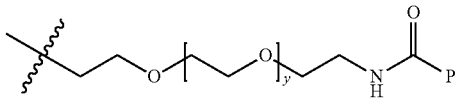

wherein, P is a $C_1$-$C_{24}$ aliphatic saturated radical or a $C_2$-$C_{24}$ aliphatic unsaturated radical, and y is an integer ranging from 0 to 3,

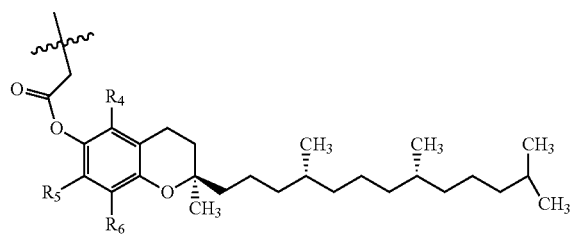

wherein, $R_4$=$R_5$=$R_6$=—$CH_3$ or $R_4$=$R_6$=—$CH_3$ and $R_5$=—H or $R_4$=—H and $R_5$=$R_6$=—$CH_3$ or $R_4$=$R_5$=—H, $R_6$=—$CH_3$,

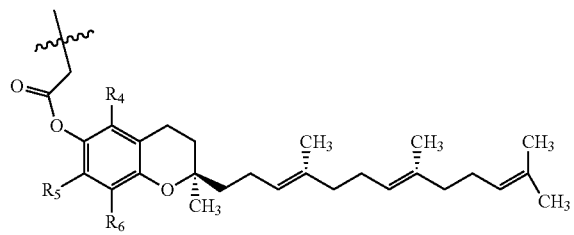

wherein, $R_7$=$R_8$=$R_9$=—$CH_3$ or $R_7$=$R_9$=—$CH_3$ and $R_8$=—H or $R_7$=—H and $R_8$=$R_9$=—$CH_3$ or $R_7$=$R_8$=—H and $R_9$=—$CH_3$,

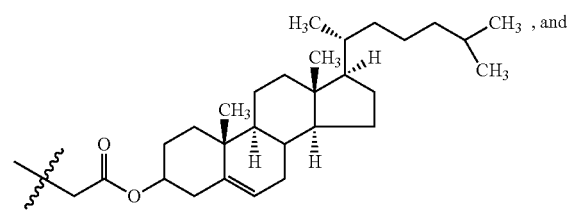

and

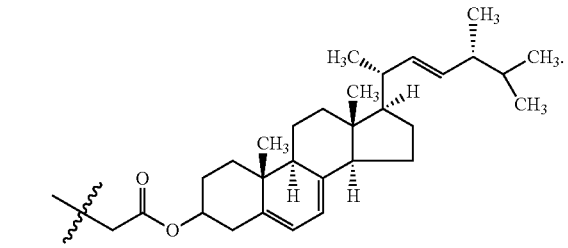

5. A compound of formula II:

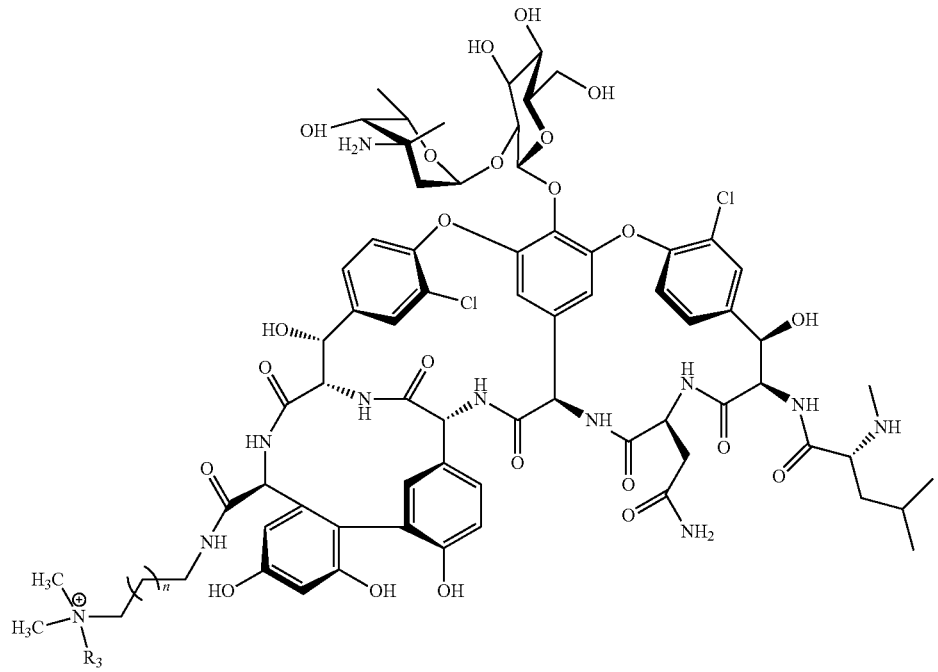

Formula II or a pharmaceutically acceptable salt thereof,
wherein, $R_3$ is an aliphatic saturated radical represented by formula $C_mH_{2m+1}$, wherein m is an integer ranging from 8 to 14, and wherein n is an integer ranging from 0 to 3;
wherein when m is 10, n is not 1; and
wherein the compound or pharmaceutically acceptable salt thereof has antibacterial activity.

6. A method for treatment of bacterial infection in a subject in need thereof comprising administering to the subject an effective amount of the compound of formula I:

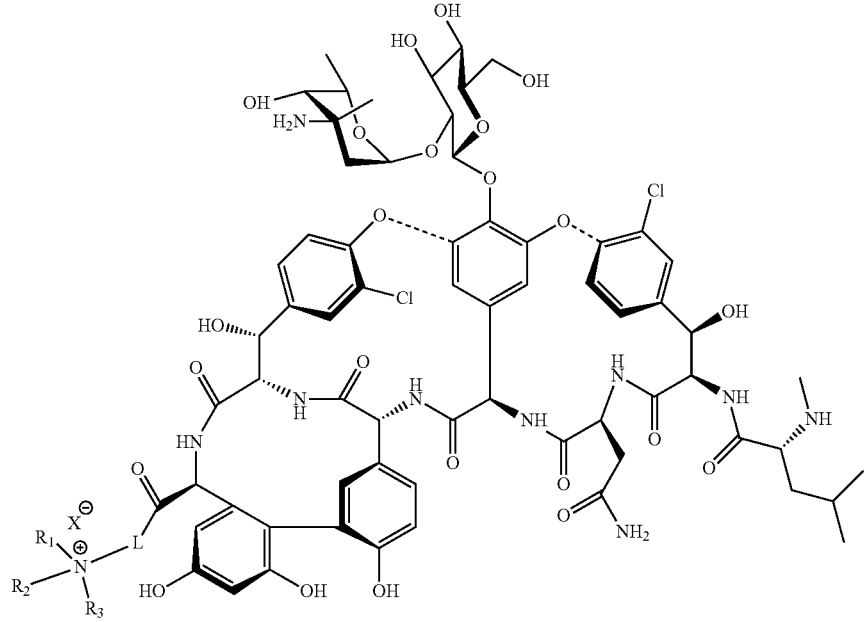

Formula I or a pharmaceutically acceptable salt thereof,
wherein,
L is a $C_2$-$C_{22}$ aliphatic radical or a $C_3$-$C_{22}$ aromatic radical linked by an amide bond to a carboxylic group;
$R_1$, $R_2$ and $R_3$ are, independently at each occurrence, a $C_1$-$C_{40}$ aliphatic radical or a $C_3$-$C_{40}$ aromatic radical; and
wherein at least one of $R_1$, $R_2$, or $R_3$ comprises at least 5 carbon atoms.

7. The method of claim 6, wherein the bacterial infection is caused by a Gram-positive bacterium or a Gram-negative bacterium.

8. The method of claim 6, wherein the bacterial infection is caused by a drug-resistant bacterium.

9. The method of claim 8, wherein the drug resistant bacterium is a vancomycin-resistant bacterium or a methicillin-resistant bacterium.

10. The method of claim 6, wherein the bacterial infection is caused by *E. coli*.

11. A method for treatment of bacterial infection in a subject in need thereof comprising administering to the subject an effective amount of the compound of claim 5.

12. The method of claim 11, wherein the bacterial infection is caused by a Gram-positive bacterium or a Gram-negative bacterium.

13. The method of claim 11, wherein the bacterial infection is caused by a drug-resistant bacterium.

14. The method of claim 13, wherein the drug resistant bacterium is a vancomycin-resistant bacterium or a methicillin-resistant bacterium.

15. The method of claim 11, wherein the bacterial infection is caused by *E. coli*.

16. A composition comprising the compound of claim 1 and a pharmaceutically acceptable carrier.

17. A composition comprising the compound of claim 5 and a pharmaceutically acceptable carrier.

18. The compound of claim 1, wherein L is a $C_3$ aliphatic radical, two of $R_1$, $R_2$, and $R_3$ are $CH_3$, and the other of $R_1$, $R_2$, and $R_3$ is selected from a group consisting of $C_8H_{17}$, $C_{14}H_{29}$, $CH_2CONHC_{10}H_{21}$, $CH_2CONHC_{12}H_{25}$, $CH_2CONHC_8H_{17}$, $CH_2CONHC_6H_{13}$, and $CH_2CONHC_{14}H_{29}$.

19. A method for treatment of bacterial infection in a subject in need thereof, the method comprising administering to the subject an effective amount of the compound of claim 18.

20. A compound of formula I:

Formula I

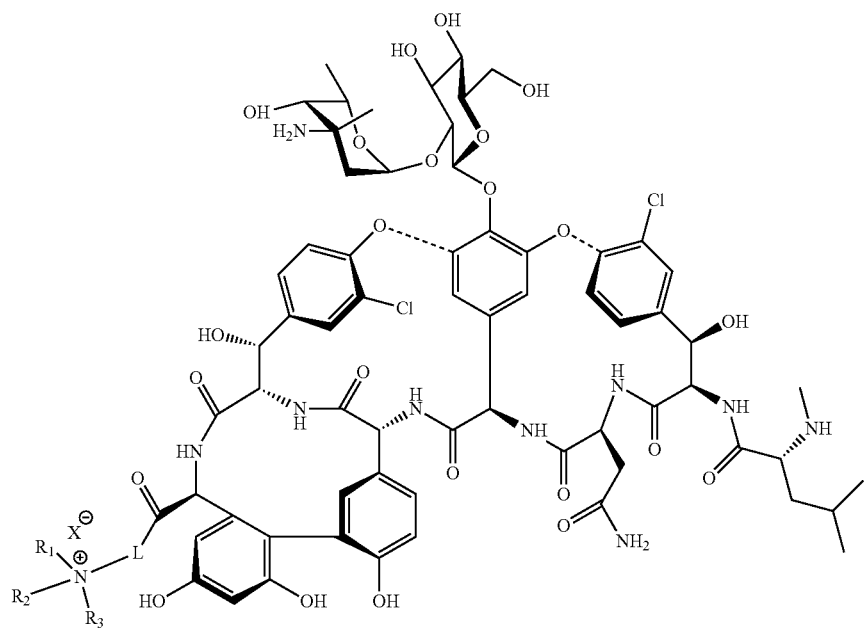

or a pharmaceutically acceptable salt thereof,
wherein,
L is a $C_3$ aliphatic radical; and
two of $R_1$, $R_2$, and $R_3$ are $CH_3$, and the other of $R_1$, $R_2$, and $R_3$ is selected from a group consisting of $C_8H_{17}$, $C_{14}H_{29}$, $CH_2CONHC_{10}H_{21}$, $CH_2CONHC_{12}H_{25}$, $CH_2CONHC_8H_{17}$, $CH_2CONHC_6H_{13}$ and $CH_2CONHC_{14}H_{29}$,
wherein the compound or pharmaceutically acceptable salt thereof has antibacterial activity.

* * * * *